US011008597B2

(12) United States Patent
Del Cardayre et al.

(10) Patent No.: US 11,008,597 B2
(45) Date of Patent: May 18, 2021

(54) CHEMO-ENZYMATIC PROCESS

(71) Applicant: Genomatica, Inc., San Diego, CA (US)

(72) Inventors: Stephen B. Del Cardayre, Belmont, CA (US); Andreas W. Schirmer, Hayward, CA (US); Myong Ko, San Mateo, CA (US); Haibo Wang, San Pablo, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 15/301,754

(22) PCT Filed: Apr. 10, 2015

(86) PCT No.: PCT/US2015/025452
§ 371 (c)(1),
(2) Date: Oct. 4, 2016

(87) PCT Pub. No.: WO2015/157719
PCT Pub. Date: Oct. 15, 2015

(65) Prior Publication Data
US 2017/0029854 A1 Feb. 2, 2017

Related U.S. Application Data

(60) Provisional application No. 61/978,176, filed on Apr. 10, 2014.

(51) Int. Cl.
| C12P 17/08 | (2006.01) |
| C12P 17/04 | (2006.01) |
| C12P 7/44 | (2006.01) |
| C12P 7/42 | (2006.01) |

(52) U.S. Cl.
CPC ............... *C12P 17/08* (2013.01); *C12P 7/42* (2013.01); *C12P 7/44* (2013.01); *C12P 17/04* (2013.01)

(58) Field of Classification Search
None
See application file for complete search history.

(56) References Cited

U.S. PATENT DOCUMENTS

| 2,234,551 | A | 3/1941 | Collaud |
| 3,681,395 | A | 8/1972 | Mookherjee et al. |
| 3,963,571 | A | 6/1976 | Bost |
| 4,014,902 | A | 3/1977 | Tseng |
| 4,709,058 | A | 11/1987 | Cahill et al. |
| 5,000,000 | A | 3/1991 | Ingram et al. |
| 5,028,539 | A | 7/1991 | Ingram et al. |
| 5,215,901 | A | 6/1993 | Boog |
| 5,424,202 | A | 6/1995 | Ingram et al. |
| 5,482,846 | A | 1/1996 | Ingram et al. |
| 5,602,030 | A | 2/1997 | Ingrahm et al. |
| 5,717,111 | A | 2/1998 | Koehler |
| 7,247,753 | B2 | 7/2007 | Wartini |
| 7,470,526 | B2* | 12/2008 | Cotticelli ............... C12P 41/00 435/126 |
| 8,097,439 | B2 | 1/2012 | Alibhai et al. |
| 8,110,093 | B2 | 2/2012 | Friedman et al. |
| 8,110,670 | B2 | 2/2012 | Hu et al. |
| 8,183,028 | B2 | 5/2012 | Alibhai et al. |
| 8,232,924 | B2 | 7/2012 | Bucca et al. |
| 8,268,599 | B2 | 9/2012 | Schirmer et al. |
| 8,283,143 | B2 | 10/2012 | Hu et al. |
| 8,313,934 | B2 | 11/2012 | Bhatia et al. |
| 8,372,610 | B2 | 2/2013 | Lee et al. |
| 8,530,221 | B2 | 9/2013 | Hu et al. |
| 2010/0242345 | A1 | 9/2010 | Keasling et al. |
| 2011/0072714 | A1 | 3/2011 | Gaertner |
| 2013/0177951 | A1* | 7/2013 | Burk ............... C07C 213/06 435/128 |
| 2017/0029854 | A1* | 2/2017 | Del Cardayre ........... C12P 7/42 |

FOREIGN PATENT DOCUMENTS

| JP | H03-219886 | 9/1991 |
| WO | WO-2008/119735 | 10/2008 |
| WO | WO-2010/127318 | 11/2010 |
| WO | WO-2013/019647 | 2/2013 |
| WO | WO-2013/039563 A1 | 3/2013 |
| WO | WO-2014/201474 | 12/2014 |

OTHER PUBLICATIONS

Communication issued on EP Application 15718726.1, dated Jul. 6, 201.
Communication issued on EP Appl. 15718726.1, dated Jan. 30, 2018.
Office Action issued on Colombian Application NC2016/0003631, dated Jan. 3, 2018, English translation only.
Arraes, Fabricio B.M. et al., "General metabolism of the dimorphic and pathogenic fungus Paracoccidioides brasiliensis", Genetics and Molecular Research, 4, (2): 290-308 (2005).
Office Action on JP Application 2016-561647, dated Mar. 25, 2019, 9 pages with translation.
Decision to Grant in JP Patent Application No. 2016-561647 dated Feb. 19, 2020 (with English translation) (5 pages).
Examination Report in in Patent Application No. 201617036588, dated Jan. 21, 2020, 6 pages with translation.
Office Action in MX Patent Application No. MX Patent Application MX/a/2016/013240, dated Jan. 14, 2020, 6 pages with translation.
Second Office Action in CN Patent Application No. 201580018870.4 dated Jul. 1, 2020 (with English translation) (14 pages).
Preliminary Office Action in BR Patent Application No. 112016023232-1 dated Dec. 3, 2019 (with English translation) (6 pages).
Mookherjee, B.D., et al., "Synthesis of Delta 9-Isoambrettolide and Its Isomers from 1,9-Cyclohexadecadiene," J. Org. Chem., 37(24): 3846-3848 (1972).

(Continued)

*Primary Examiner* — Hope A Robinson
(74) *Attorney, Agent, or Firm* — Harness Dickey & Pierce P.L.C.

(57) ABSTRACT

The present disclosure relates to processes that combine microbial production of organic intermediates and subsequent synthetic transformation to provide compounds of industrial value, including compounds used in fragrances.

8 Claims, No Drawings

(56) References Cited

OTHER PUBLICATIONS

Extended European Search Report from corresponding European Application No. 20171012.6 dated Oct. 2, 2020.
Chatterjea, J., et al., "Phosphonium Iodide in Organic Synthesis," Indian Journal of Chemistry, vol. 23B, p. 733-735 (1984).
Hunsdiecker, H., "Synthesis of the cis- and trans- forms of an Isoambrettolides and the Civetones," Naturwissenschaften, vol. 38/39, p. 587 (1942).
Official Action issued on Colombian Appl. NC2016/003631, dated May 16, 2018, English Translation only.
Altschul et al. "Basic Local Alignment Search Tool," (1990) J. Mol. Biol. 215(3):403-410.
Altschul et al. "Protein Database Searches Using Compositionally Adjusted Substitution Matrices," (2005) FEBS J. 272(20):5101-5109.
Baldari et al., "A novel leader peptide which allows efficient secretion of a fragment of human interleukin 1 beta in *Saccharomyces cerevisiae*," EMBO J. 6(1): 229-234 (1987).
Caviglia et al., Rat Long Chain Acyl-CoA Synthetase 5, but Not 1, 2, 3, or 4, Complements *Escherichia coli* fadD*, The Journal of Biological Chemistry, 279(12): 1163-1169 (2004).
Cronan et al. "FadR, transcriptional co-ordination of metabolic expediency," (1998) Mole. Microbiol. 29(4):937-943.
Funhoff et al., "CYP153A6, a Soluble P450 Oxygenase Catalyzing Terminal-Alkane Hydroxylation," J. Bacteriol. 188(14): 5220-5227 (2006).
Honda-Malca et al., "Bacterial CYP153A monooxygenases for the synthesis of omega-hydroxylated fatty acids," Chem. Commun. 48: 5115-5117 (2012).
Inanga et al., "A Rapid Esterification by Means of Mixed Anhydride and Its Application to Large-ring Lactonization," Bulletin of the Chemical Society of Japan, vol. 52, No. 7, 1979 pp. 1969-1973.
International Search Report issued on PCT/US2015/0825452, dated Jul. 9, 2015.
Isbell et al., "A Highly Regioselective Synthesis of Lactones from Meadowfoam Fatty Acids", JAOCS, vol. 74, No. 2, 1997, pp. 153-158.
Kurjan et al., "Structure of a Yeast Pheromone Gene (MFα): A Putative α-Factor Precursor Contains Four Tandem Copies of Mature α-Factor," Cell 30: 933-943 (1982).
Lucklow et al., "High level expression of nonfused foreign genes with Autographa califomica nuclear polyhedrosis virus expression vectors," Virology 170(1): 31-39 (1989).
Maniatis et al., "Regulation of Inducible and Tissue-Specific Gene Expression," Science 236: 1237-1245 (1987).
Mulzer et al., "Stereospecific Synthesis of y-Lactones by Dyotropic Wagner-Meerwein Rearrangement," Angew Chem. Int. Ed. Engl 18 (1979) No. 10, pp. 793-794.
Needleman et al., "A General Method Applicable to the Search for Similarities in the Amino Acid Sequence of Two Proteins," J. Mol. Biol. 48:444-453 (1970).
Omelchenko et al., "Non-homologous isofunctinal enzymes: A systematic analysis of alterntive solutions in enzyme evolution," (2010) Biol. Direct 5, 20 pages.
Rosenberg, "Multiple Sequence Alignment Accuracy and Evolutionary Distance Estimation," BMC Bioinformatics 6: 278 (2005).
Scheps et al., "Regioselective omega-hydroxylation of medium-chain n-alkanes and primary alcohols by CYP153 enzymes from Mycobacterium marinum and *Polaromonas* sp. strain JS666," Org. Biomol. Chem. 9: 6727-6733 (2011).
Schultz et al., "Expression and secretion in yeast of a 400-kDa envelope glycoprotein derived from Epstein-Barr virus," Gene 54: 113-123 (1987).
Smith et al., "Production of Human Beta Interferon in Insect Cells Infected with a Vaculovirus Expression Vector," Mol. Cell Biol. 3(12): 2156-2165 (1983).
Spanagel et al., "Macrocyclic Esters", (1935) J. Am. Chem. Soc., 57:929-934.
Van Beilen, "Cytochrome P450 Alkane Hydroxylases of the CYP153 Family Are Common in Alkane-Degrading Eubacteria Lacking Integral Membrane Alkane Hydroxylases," Appl. Environ. Microbiol. 72(1): 59-65 (2006).
Vandamme et al., "Bioflavours and Fragrances via fermentation and biocatalysis," Journal of Chemical Technology and Biotechnology, vol. 77, No. 12, Dec. 1, 2012, pp. 1323-1332.
Vandamme et al., Bioflavours and fragrances via fermentation and biocatalysis, Journal of Chemical Technology and Biotechnology, vol. 77, 2002, pp. 1323-1332.

\* cited by examiner

CHEMO-ENZYMATIC PROCESS

CROSS-REFERENCE TO RELATED APPLICATIONS

This application is a 35 U.S.C. § 371 National Phase Application of PCT/US2015/025452, filed Apr. 10, 2015, which claims the benefit of U.S. Provisional Application No. 61/978,176 filed Apr. 10, 2014, the contents of which are hereby incorporated-by-reference in their entireties.

FIELD

The disclosure relates to processes combining biosynthetic production of organic intermediates and subsequent synthetic transformation to provide compounds of industrial value.

BACKGROUND

Fatty acid derivatives have many commercial uses as components of industrial agents. However, purely chemical methods of producing them may require the use of hazardous reagents and/or may be either energy intensive or environmentally unfriendly. Conversely, existing purely fermentative routes from petrochemicals or oleochemical feedstocks may still be too costly in comparison to the chemical methods of production and are limited in the types of products that can be made.

The current supply of fragrance ingredients is based on three routes: (i) extraction from plants or animals, (ii) total chemical synthesis from petrochemicals, and (iii) fungal biotransformation of oleochemicals. A fragrance obtained from a plant or animal is considered a natural fragrance and as such is in high consumer demand and commands premium prices. However, supply is limited as these fragrance compounds usually exist only in minute quantities in sometimes rare plants or wild animals, and they are also in strong dependence on factors which are difficult to control, for example the influence of weather and the risk of plant disease. By far the most prevalent route to fragrance ingredients is the total chemical synthesis from petrochemical precursors and the extraction and refinement of natural materials. Although such fragrances circumvent the supply issue of natural fragrances, they are synthetic and not considered natural by the consumer and in addition are not identical in structure to the natural fragrances in most cases, e.g., natural ambrettolide vs. synthetic isoambrettolide. Fragrance compounds derived from fungal biotransformation can be considered natural, but they are rather marginal as they use expensive oleochemical feedstocks and the number of fragrance compounds accessible by this method is limited.

In contrast, the present chemo-enzymatic method via microbially-derived fatty acid derivatives from carbon-based feedstocks can produce a large variety of natural fragrance ingredients in significant quantities by using a controlled and cost-efficient process. Such fragrance ingredients are natural, because they are derived from living organisms, i.e., microbes, using carbon-based feedstocks.

SUMMARY

In some aspects, embodiments disclosed herein relate to chemo-enzymatic processes for creating a fragrance ingredient, including culturing a recombinant microorganism that encompasses one or more metabolic modifications including one or more altered enzymatic functionalities, the microorganism producing at least one type of fatty acid derivative in vivo, wherein the culturing is performed with a carbon-based feedstock, and contacting the fatty acid derivative ex vivo with a reagent under conditions sufficient to produce a lactone or macrocyclic ketone. In one embodiment, the carbon-based feedstock encompasses a simple carbon source. In another embodiment, the carbon-based feedstock encompasses a renewable carbon source.

One aspect of the disclosure provides a chemo-enzymatic process for creating a fragrance ingredient, including culturing a recombinant microorganism having a metabolic modification, the microorganism producing at least one type of fatty acid derivative in vivo, wherein the culturing is performed with a carbon-based feedstock; and contacting the fatty acid derivative ex vivo with a reagent under conditions sufficient to produce a lactone or macrocyclic ketone. In one aspect, the metabolic modification includes an altered enzymatic functionality. In one embodiment, the altered enzymatic functionality includes a thioesterase of E.C. 3.1.2.- or E.C. 2.1.1.5. In another embodiment, the altered enzymatic functionality includes both a thioesterase of E.C. 3.1.2.- or E.C. 2.1.1.5 and an ester synthase of E.C. 2.3.1.20. In another embodiment, the altered enzymatic functionality includes an omega-hydroxylase or oxygenase of E.C. 1.14.15.3. In still another embodiment, the altered enzymatic functionality includes both an omega-hydroxylase or oxygenase of E.C. 1.14.15.3 and an oxidase or dehydrogenase of EC 1.1.1.1/2, EC 1.1.3.13, EC 1.1.3.20, EC 1.2.1.3/4/5 or EC 1.2.3.1. In another embodiment, the metabolic modification increases saturated or unsaturated fatty acid derivatives within the microorganism. In another embodiment, the fatty acid derivative has an odd-numbered carbon chain, methyl-branching, or combinations thereof. In yet another embodiment, the fragrance ingredient is a lactone or a macrocyclic ketone. In another embodiment, the fragrance ingredient is a gamma-lactone (γ-lactone), a delta-lactone (δ-lactone), or combinations thereof. In still another embodiment, the fragrance ingredient is a $C_8$ to $C_{18}$ macrolactone.

Another aspect of the disclosure provides a chemo-enzymatic process (supra) that further includes isolating the fatty acid derivative prior to the contacting step. In one embodiment, the contacting step includes dehydration, lactonization, or combinations thereof. In another aspect, at least one type of fatty acid derivative is secreted from the recombinant microorganism and the contacting step is performed without isolating the fatty acid derivative from the culturing step. In one embodiment, the reagent includes a protic acid including, but not limited to, hydrochloric acid, sulfuric acid, phosphoric acid and recoverable resin acids. In another embodiment, the agent is a Lewis acid including, but not limited to, an organostannane transesterification catalyst, copper or zinc salts, silver triflate, and zeolites. In still another embodiment, the reagent is a peptide coupling agent.

Another aspect of the disclosure provides a chemo-enzymatic process (supra), wherein the type of fatty acid derivative includes, but is not limited to, an unsaturated fatty acid, an unsaturated fatty acid ester, an omega-hydroxy fatty acid (ω-OH FA), an omega-hydroxy unsaturated fatty acid (unsaturated ω-OH FA), an omega-hydroxy fatty acid ester (ω-OH fatty acid ester), an omega-hydroxy unsaturated fatty acid ester (unsaturated ω-OH fatty acid ester), a 3-hydroxy fatty acid (3-OH FA), a 3-hydroxy unsaturated fatty acid (unsaturated 3-OH FA), a 3-hydroxy fatty acid ester (3-OH fatty acid ester), a 3-hydroxy unsaturated fatty acid ester (unsaturated 3-OH fatty acid ester), an alpha-omega-diacid (α,ω-diacid), an unsaturated alpha-omega diacid (unsaturated α,ω-diacid), an alpha-omega-diacid ester (α,ω-diacid ester), an unsaturated alpha-omega-diacid ester (unsaturated α,ω-diacid ester), and combinations thereof. In one embodiment, the unsaturated fatty acid is monounsaturated. In another embodiment, the unsaturated fatty acid ester is monounsaturated. In another embodiment, the unsaturated fatty acid ester includes an unsaturated fatty acid methyl ester (FAME) and an unsaturated fatty acid ethyl ester (FAEE). In another embodiment, the unsaturated FAME or FAEE is monounsaturated. In another embodiment, the omega-hydroxy unsaturated fatty acid (unsaturated ω-OH FA) is monounsaturated. In another embodiment, the unsaturated fatty acid ester includes an unsaturated fatty acid methyl ester (FAME) and an unsaturated fatty acid ethyl ester (FAEE). In another embodiment, the 3-hydroxy fatty acid ester (3-OH fatty acid ester) is a 3-hydroxy fatty acid methyl ester (3-OH FAME) or a 3-hydroxy fatty acid ethyl ester (3-OH FAEE). In another embodiment, the omega-hydroxy fatty acid ester (ω-OH fatty acid ester) is an omega-hydroxy fatty acid methyl ester (ω-OH FAME) or an omega-hydroxy fatty acid ethyl ester (ω-OH FAEE). In another embodiment, the omega-hydroxy unsaturated fatty acid ester (unsaturated ω-OH fatty acid ester) is monounsaturated. In another embodiment the monounsaturated omega-hydroxy fatty acid ester (monounsaturated ω-OH fatty acid ester) includes, but is not limited to, an omega-hydroxy monounsaturated fatty acid methyl ester (ω-OH monounsaturated FAME) and an omega-hydroxy monounsaturated fatty acid ethyl ester (ω-OH monounsaturated FAEE). In another embodiment, the 3-hydroxy unsaturated fatty acid (unsaturated 3-OH FA) is monounsaturated. In another embodiment, the 3-hydroxy fatty acid ester (3-OH fatty acid ester) is a 3-hydroxy fatty acid methyl ester (3-OH FAME) or a 3-hydroxy fatty acid ethyl ester (3-OH FAEE). In another embodiment, the 3-hydroxy unsaturated fatty acid ester (unsaturated 3-OH fatty acid ester) is monounsaturated. In another embodiment, the monounsaturated 3-hydroxy fatty acid ester (3-OH fatty acid ester) is a 3-hydroxy monounsaturated fatty acid methyl ester (monounsaturated 3-OH FAME) or a 3-hydroxy monounsaturated fatty acid ethyl ester (monounsaturated 3-OH FAEE). In another embodiment, the unsaturated alpha-omega-diacid (unsaturated α,ω-diacid) or the unsaturated alpha-omega-diacid ester (unsaturated α,ω-diacid ester) is monounsaturated. In another embodiment, the monounsaturated alpha-omega-diacid ester (monounsaturated α,ω-diacid ester) is a half-acid ester. In another embodiment, the half-acid ester is a methyl or ethyl ester. In another embodiment, the monounsatured alpha-omega-diacid ester (monounsaturated α,ω)-diacid ester) is a diester. In still another embodiment, the diester is a methyl diester or an ethyl diester.

DETAILED DESCRIPTION

Embodiments disclosed herein are directed, in part, to processes that combine the culturing of recombinant microorganisms capable of synthesizing fatty acid derivatives using engineered biosynthetic pathways with synthetic organic chemistry transformations to provide efficient preparation of delta (δ) and gamma (γ) lactones, or macrocyclic lactone- and macrocyclic ketone products. Particularly, the processes provide for the production of advanced intermediate compounds from renewable biomass derived materials (i.e., renewable feedstock), such as carbohydrates from corn, cane, or lignocellulosic biomass; or waste products such as glycerol, flu-gas, syn-gas; or the reformation of organic materials such as biomass or natural gas or carbon dioxide. This provides cost effective and renewable alternative sources for the production of these important chemicals. Because the processes provide advanced compounds with good selectively from simple renewable feedstock there are economic advantages in terms of cost, operation simplicity and environmental benefit, when compared to conventional synthetic multistep chemical synthesis.

Recombinant microorganisms disclosed herein can be engineered to produce commercial quantities of a variety of different fatty acid derivatives having different chain lengths between $C_8$ and $C_{18}$ or more carbon atoms, including even, odd chains or methyl-branched chains, and with varied derivative functionality including, unsaturation, hydroxylation, and esterification. In some embodiments, the recombinant microorganisms disclosed herein are capable of secreting the resultant fatty acid derivatives into the culture media or fermentation broth to facilitate synthetic manipulation in situ without isolation from the culture or to simplify product isolation. Production of fatty acid derivatives via the engineered pathways in the recombinant microorganisms disclosed herein is useful because it may result in higher product yields than through naturally occurring biosynthetic pathways or via conventional synthetic organic chemistry techniques.

Definitions

As used in this specification and the appended claims, the singular forms "a," "an" and "the" include plural referents unless the context clearly dictates otherwise. Thus, for example, reference to "a host cell" includes two or more such host cells, reference to "a fatty acid" includes one or more fatty acids, or mixtures of fatty acids, reference to "a nucleic acid sequence" includes one or more nucleic acid sequences, reference to "an enzyme" includes one or more enzymes, and the like.

The term "fragrance ingredient" means, for the purpose of the specification and claims, a material that can be used alone or be added to a mixture or composition of essential oils and/or aroma compounds and/or fixatives and/or solvents to create a fragrance or perfume. The fragrance or perfume is used to add a pleasant scent to a human body, an animal, a food group, an object, and/or a living space. A lactone (including a macrolactone) and a macrocyclic ketone are examples of fragrance ingredients. Other fragrance ingredients are listed on the website of the International Fragrance Association (IFRA) at the World Wide Web at ifraorg.org.

A "macrolactone" is any macrocyclic lactone. In one embodiment, a macrolactone is a lactone with >10 atoms in the ring.

A "half-acid ester" is used interchangeably with "a half ester of a dicarboxylic acid", which is a dicarboxylic acid that has one of its carboxylic groups esterified.

As used herein, the terms "microbial," "microbial organism" or "microorganism" is intended to mean any organism that exists as a microscopic cell or single celled organism that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

The term "recombinant microorganism" refers to a host cell that has been genetically modified such that, for example, certain enzymatic activities within the host cell have been altered, added and/or deleted relative to the parent cell or native host cell. A genetically modified host cell is an example of a recombinant microorganism. As such, a "modified or altered level of activity of a protein", for example an enzyme, in a recombinant host cell refers to a difference in one or more characteristics in the activity determined relative to the parent or native host cell in which that same modification is absent. Typically differences in activity are determined between a recombinant host cell, having modified activity, and the corresponding wild-type host cell (e.g., comparison of a culture of a recombinant host cell relative to the corresponding wild-type host cell), not having that modified activity. Modified activities can be the result of, for example, modified amounts of protein expressed by a recombinant host cell (e.g., as the result of increased or decreased number of copies of DNA sequences encoding the protein, increased or decreased number of mRNA transcripts encoding the protein, and/or increased or decreased amounts of protein translation of the protein from mRNA); changes in the structure of the protein (e.g., changes to the primary structure, such as, changes to the protein's coding sequence that result in changes in substrate specificity, changes in observed kinetic parameters); and changes in protein stability (e.g., increased or decreased degradation of the protein). In some embodiments, the polypeptide is a mutant or a variant of any of the polypeptides described herein. In certain instances, the coding sequences for the polypeptides described herein are codon optimized for expression in a particular host cell. For example, for expression in *E. coli*, one or more codons can be optimized (see, e.g., Grosjean et al. (1982) *Gene* 18:199-209).

The term "fatty acid" means a carboxylic acid having the formula RCOOH. R represents an aliphatic group, preferably an alkyl group. R can comprise between about 4 and about 22 carbon atoms. Fatty acids can have a branched chain or straight chain and may be saturated, monounsaturated, or polyunsaturated.

A "fatty acid derivative" is a product made in part from the fatty acid biosynthetic pathway of the production host organism, and in part from acyl-ACP or acyl-CoA. The term is intended to encompass any fatty acid ($C_6$ to $C_{24}$ which has additional chemical functionality and can include derivatives $C_6$-$C_{35}$). A fatty acid derivative may possess one or more of an unsaturation, hydroxylation, beta and omega hydroxylation, and/or esterification. Exemplary fatty acid derivatives include saturated or monounsaturated fatty acids or esters, omega hydroxylated fatty acids or esters, and the like. Additional exemplary fatty acid derivatives include, acyl-CoA, fatty acids, fatty aldehydes, short and long chain alcohols, fatty alcohols, hydrocarbons, esters (e.g., waxes, fatty acid esters, fatty esters), terminal olefins, internal olefins, and ketones.

As used herein, the term "metabolic modification" is intended to refer to a change in a metabolic or biosynthetic pathway so that it differs from its naturally occurring state. Metabolic modifications can include, for example, elimination or attenuation of a biochemical reaction activity by functional disruptions of one or more genes encoding an enzyme participating in the reaction. It can also include an increase of a biochemical reaction activity by upregulating or overexpressing one or more genes encoding an enzyme participating in the reaction. It can also include the introduction of a biochemical reaction activity by exogenously expressing one or more genes encoding an enzyme participating in the reaction. Such modifications can be achieved through the genetic, physical, or chemical manipulation of a microorganism or its environment.

The term "altered enzymatic functionality" refer to an enzymatic activity that is not naturally present in the cell. An example of an altered enzymatic functionality is an exogenously expressed gene that codes for a protein with enzymatic activity that is not naturally found in the cell. Another example of an altered enzymatic functionality is an overexpressed gene that codes for a protein with enzymatic activity that is not naturally found in the cell at the increased expression level.

The term "producing a fatty acid derivative in vivo", as used herein, means producing a fatty acid derivative in viable and/or genetically modified host cells from a renewable feedstock such as a carbohydrate or others, wherein the renewable feedstock is added to a fermentation broth as a carbon source so that the host cells can take up and metabolize the carbon source during fermentation. This differs from methods where fatty acid derivatives are produced in vitro, wherein purified enzymes or cell lysates are being used and the direct substrate for the enzymatic conversion, e.g., a fatty acid or fatty acid derivative, is being added to the purified enzyme or to the cell lysate solutions. This also differs from methods where fatty acid derivatives are produced in biotransformations, wherein resting cells are being used and the direct substrate for the enzymatic conversion, e.g., a fatty acid or fatty acid derivative, is being exogenously added to the resting cells.

As used herein, the term "fatty acid biosynthetic pathway" means a biosynthetic pathway that produces fatty acids and fatty acid derivatives. Examples of such fatty acid derivatives include, without limitation, ω-hydroxylated fatty acid and ester derivatives, ω-unsaturated fatty acid and ester derivatives, and 3-hydroxy fatty acid and ester derivatives. The fatty acid biosynthetic pathway may include additional enzymes or polypeptides with enzymatic activities besides the ones discussed herein to produce fatty acid derivatives such as ω-hydroxylated fatty acid and ester derivatives, ω-unsaturated fatty acid and ester derivatives, and 3-hydroxy fatty acid and ester derivatives having the desired characteristics.

Enzyme Classification (EC) Numbers are established by the Nomenclature Committee of the International Union of Biochemistry and Molecular Biology (IUBMB), a description of which is available on the IUBMB Enzyme Nomenclature website on the World Wide Web. EC numbers classify enzymes according to the enzyme-catalyzed reactions. For example, if different enzymes (e.g., from different organisms) catalyze the same reaction, then they are classified under the same EC number. In addition, through convergent evolution, different protein folds can catalyze identical reactions and therefore are assigned identical EC numbers (see Omelchenko et al. (2010) *Biol. Direct* 5:31). Proteins that are evolutionarily unrelated and can catalyze the same biochemical reactions are sometimes referred to as analogous enzymes (i.e., as opposed to homologous enzymes). EC numbers differ from, for example, UniProt identifiers which specify a protein by its amino acid sequence.

The term "accession number" or "NCBI accession number" or "GenBank accession number" refers to a number that denotes a specific nucleic acid sequence. Sequence accession numbers that are discussed in this description were obtained from databases provided by the NCBI (National Center for Biotechnology Information) maintained by the National Institutes of Health, U.S.A., and from the UniProt Knowledgebase (UniProtKB) and Swiss-Prot databases provided by the Swiss Institute of Bioinformatics (also referred to as UniProtKB accession number).

As used herein, the term "nucleotide" refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates, and the like).

As used herein, the term "polynucleotide" refers to a polymer of ribonucleotides (RNA) or deoxyribonucleotides (DNA), which can be single-stranded or double-stranded and which can contain non-natural or altered nucleotides. The terms "polynucleotide," "nucleic acid sequence," and "nucleotide sequence" are used interchangeably herein to refer to a polymeric form of nucleotides of any length, either RNA or DNA. These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides. The polynucleotide can be in any form, including but not limited to, plasmid, viral, chromosomal, EST, cDNA, mRNA, and rRNA.

As used herein, the terms "polypeptide" and "protein" are used interchangeably to refer to a polymer of amino acid residues. The term "recombinant polypeptide" refers to a polypeptide that is produced by recombinant techniques, wherein generally DNA or RNA encoding the expressed protein is inserted into a suitable expression vector that is in turn used to transform a host cell to produce the polypeptide.

As used herein, the terms "homolog," and "homologous" refer to a polynucleotide or a polypeptide comprising a sequence that is at least about 50% identical to the corresponding polynucleotide or polypeptide sequence. Preferably homologous polynucleotides or polypeptides have polynucleotide sequences or amino acid sequences that have at least about 80%, 81%, 82%, 83%, 84%, 85%, 86%, 87%, 88%, 89%, 90%, 91%, 92%, 93%, 94%, 95%, 96%, 97%, 98% or at least about 99% homology to the corresponding amino acid sequence or polynucleotide sequence. As used herein the terms sequence "homology" and sequence "identity" are used interchangeably. One of ordinary skill in the art is well aware of methods to determine homology between two or more sequences. Briefly, calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a first sequence that is aligned for comparison purposes is at least about 30%, preferably at least about 40%, more preferably at least about 50%, even more preferably at least about 60%, and even more preferably at least about 70%, at least about 75%, at least about 80%, at least about 85%, at least about 90%, at least about 95%, or about 100% of the length of a second sequence. The amino acid residues or nucleotides at corresponding amino acid positions or nucleotide positions of the first and second sequences are then compared. When a position in the first sequence is occupied by the same amino acid residue or nucleotide as the corresponding position in the second sequence, then the molecules are identical at that position. The percent homology between the two sequences is a function of the number of identical positions shared by the sequences, taking into account the number of gaps and the length of each gap, that need to be introduced for optimal alignment of the two sequences. The comparison of sequences and determination of percent homology between two sequences can be accomplished using a mathematical algorithm, such as BLAST (Altschul et al. (1990) *J. Mol. Biol.* 215(3): 403-410). The percent homology between two amino acid sequences also can be determined using the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch, (1970) *J. Mol. Biol.* 48:444-453). The percent homology between two nucleotide sequences also can be determined using the GAP program in the GCG software package, using a NWSgapdnaCMP matrix and a gap weight of 40, 50, 60, 70, or 80 and a length weight of 1, 2, 3, 4, 5, or 6.

One of ordinary skill in the art can perform initial homology calculations and adjust the algorithm parameters accordingly. A preferred set of parameters (and the one that should be used if there is uncertainty about which parameters should be applied to determine if a molecule is within a homology limitation of the claims) are a Blossum 62 scoring matrix with a gap penalty of 12, a gap extend penalty of 4, and a frameshift gap penalty of 5. Additional methods of sequence alignment are known in the biotechnological arts (see, e.g., Rosenberg (2005) *BMC Bioinformatics* 6:278); Altschul et al. (2005) *FEBS J.* 272(20): 5101-5109).

An "ortholog" is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor. Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the growth-coupled production of a biochemical product, those skilled in the art will understand that the orthologous gene harboring the metabolic activity to be disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of *mycoplasma* 5'-3' exonuclease and *Drosophila* DNA polymerase III activity. The DNA polymerase from the first species can be considered an ortholog to either or both of the exonuclease or the polymerase from the second species and vice versa.

By contrast, "paralogs" are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, w-evolved from a common ancestor, that catalyze distinct reactions and have distinct functions in the same species. Paralogs are proteins from the same species with significant sequence similarity to each other suggesting that they are homologous, or related through w-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene compared to a gene encoding the function sought to be substituted. Therefore, a nonorthologous gene includes, for example, a paralog or an unrelated gene.

Therefore, in identifying and constructing the non-naturally occurring microbial organisms disclosed herein for production of fatty acid derivatives, those skilled in the art will understand applying the teaching and guidance provided herein to a particular species that the identification of metabolic modifications should include identification and disruption of orthologs. To the extent that paralogs and/or nonorthologous gene displacements are present in the referenced microorganism that encode an enzyme catalyzing a similar or substantially similar metabolic reaction, those skilled in the art also can disrupt these evolutionarily related genes to ensure that any functional redundancy in enzymatic activities do not short circuit the designed metabolic modifications. Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compared and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarly to determine relatedness are computed based on well-known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences. Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications and updates can be made to the above parameters to either increase or decrease the stringency of the comparison, for example, and determine the relatedness of two or more sequences.

The term "heterologous" generally means derived from a different species or derived from a different organism. As used herein it refers to a nucleotide sequence or a polypeptide sequence that is not naturally present in a particular organism. Heterologous expression means that a protein or polypeptide is experimentally added to a cell that does not normally express that protein. As such, heterologous refers to the fact that a transferred protein was initially derived from a different cell type or a different species then the recipient. For example, a polynucleotide sequence endogenous to a plant cell can be introduced into a bacterial host cell by recombinant methods, and the plant polynucleotide is then a heterologous polynucleotide in a recombinant bacterial host cell.

An "endogenous" polypeptide refers to a polypeptide encoded by the genome of the host cell (e.g., parental microbial cell) from which the recombinant cell is engineered or derived. Therefore, the term "endogenous" refers to a referenced molecule or activity that is naturally present in the host. Similarly, the term when used in reference to expression of an encoding nucleic acid refers to expression of an encoding nucleic acid contained within the natural microbial organism.

An "exogenous" polypeptide refers to a polypeptide which is not encoded by the genome of the parental microbial cell. A variant (e.g., mutant) polypeptide is an example of an exogenous polypeptide. "Exogenous" is intended to mean that the referenced molecule or the referenced activity is introduced into the host microbial organism. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Accordingly, exogenous expression of an encoding nucleic acid of the disclosure can utilize either or both a heterologous or homologous encoding nucleic acid.

As used herein, the term "fragment" of a polypeptide refers to a shorter portion of a full-length polypeptide or protein ranging in size from four amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

As used herein, the term "mutagenesis" refers to a process by which the genetic information of an organism is changed in a stable manner. Mutagenesis of a protein encoding nucleic acid sequence produces a mutant protein. Mutagenesis also refers to changes in non-coding nucleic acid sequences that result in modified protein activity.

As used herein, the term "gene" refers to a nucleic acid sequence encoding either an RNA product or a protein product, as well as operably-linked nucleic acid sequences affecting the expression of the RNA or protein (e.g., such sequences include but are not limited to promoter or enhancer sequences) or operably-linked nucleic acid sequences encoding sequences that affect the expression of the RNA or protein (e.g., such sequences include, but are not limited to, ribosome binding sites or translational control sequences).

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al. (1987) *Science* 236:1237-1245). Exemplary expression control sequences are described in, for example, Goeddel, Gene Expression Technology: Methods in Enzymology, Vol. 185, Academic Press, San Diego, Calif. (1990). In the methods of the disclosure, an expression control sequence is operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

As used herein, the term "vector" refers to a nucleic acid molecule capable of transporting another nucleic acid, i.e., a polynucleotide sequence, to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids," which refer generally to circular double stranded DNA loops that, in their vector form, are not bound to the chromosome. The terms "plasmid" and "vector" are used interchangeably herein, in as much as a plasmid is the most commonly used form of vector. However, also included are such other forms of expression vectors that serve equivalent functions and that become known in the art subsequently hereto. In some embodiments, a recombinant vector further comprises a promoter operably linked to the polynucleotide sequence. In some embodiments, the promoter is a developmentally-regulated, an organelle-specific, a tissue-specific, an inducible, a constitutive, or a cell-specific promoter. The recombinant vector typically comprises at least one sequence including (a) an expression control sequence operatively coupled to the polynucleotide sequence; (b) a selection marker operatively coupled to the polynucleotide sequence; (c) a marker sequence operatively coupled to the polynucleotide sequence; (d) a purification moiety operatively coupled to the polynucleotide sequence; (e) a secretion sequence operatively coupled to the polynucleotide sequence; and (f) a targeting sequence operatively coupled to the polynucleotide sequence. In certain embodiments, the nucleotide sequence is stably incorporated into the genomic DNA of the host cell, and the expression of the nucleotide sequence is under the control of a regulated promoter region. The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein. Expression of genes encoding polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes: (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. In certain embodiments, a polynucleotide sequence of the disclosure may be operably linked to a promoter derived from bacteriophage T5. In certain embodiments, the host cell is a yeast cell, and the expression vector is a yeast expression vector. Examples of vectors for expression in yeast *S. cerevisiae* include pYepSec1 (Baldari et al. (1987) *EMBO J.* 6:229-234), pMFa (Kurjan et al. (1982) *Cell* 30: 933-943), pJRY88 (Schultz et al. (1987) *Gene* 54: 113-123), pYES2 (Invitrogen Corp., San Diego, Calif.), and picZ (Invitrogen Corp., San Diego, Calif.). In other embodiments, the host cell is an insect cell, and the expression vector is a baculovirus expression vector. Baculovirus vectors available for expression of proteins in cultured insect cells (e.g., Sf9 cells) include, for example, the pAc series (Smith et al. (1983) *Mol. Cell Biol.* 3:2156-2165) and the pVL series (Lucklow et al. (1989) *Virology* 170:31-39). In yet another embodiment, the polynucleotide sequences described herein can be expressed in mammalian cells using a mammalian expression vector. Other suitable expression systems for both prokaryotic and eukaryotic cells are well known in the art; see, e.g., Sambrook et al., "Molecular Cloning: A Laboratory Manual," second edition, Cold Spring Harbor Laboratory, (1989).

As used herein "acyl-CoA" refers to an acyl thioester formed between the carbonyl carbon of alkyl chain and the sulfhydryl group of the 4'-phosphopantethionyl moiety of coenzyme A (CoA), which has the formula R—C(O)S-CoA, where R is any alkyl group having at least 4 carbon atoms.

As used herein "acyl-ACP" refers to an acyl thioester formed between the carbonyl carbon of alkyl chain and the sulfhydryl group of the phosphopantetheinyl moiety of an acyl carrier protein (ACP). The phosphopantetheinyl moiety is post-translationally attached to a conserved serine residue on the ACP by the action of holo-acyl carrier protein synthase (ACPS), a phosphopantetheinyl transferase. In some embodiments an acyl-ACP is an intermediate in the synthesis of fully saturated acyl-ACPs. In other embodiments an acyl-ACP is an intermediate in the synthesis of unsaturated acyl-ACPs. In some embodiments, the carbon chain will have about 5, 6, 7, 8, 9, 10, 11, 12, 13, 14, 15, 16, 17, 18, 19, 20, 21, 22, 23, 24, 25, or 26 carbons. Each of these acyl-ACPs are substrates for enzymes that convert them to fatty acid derivatives.

As used herein, the term "clone" typically refers to a cell or group of cells descended from and essentially genetically identical to a single common ancestor, for example, the bacteria of a cloned bacterial colony arose from a single bacterial cell.

The term "regulatory sequences" as used herein typically refers to a sequence of bases in DNA, operably-linked to DNA sequences encoding a protein that ultimately controls the expression of the protein. Examples of regulatory sequences include, but are not limited to, RNA promoter sequences, transcription factor binding sequences, transcription termination sequences, modulators of transcription (such as enhancer elements), nucleotide sequences that affect RNA stability, and translational regulatory sequences (such as, ribosome binding sites (e.g., Shine-Dalgarno sequences in prokaryotes or Kozak sequences in eukaryotes), initiation codons, termination codons).

As used herein, the term "culture" typical refers to a liquid media comprising viable cells. In one embodiment, a culture includes cells reproducing in a predetermined culture media under controlled conditions, for example, a culture of recombinant host cells grown in liquid media comprising a selected carbon source and nitrogen. "Culturing" or "cultivation" refers to growing a population of recombinant host cells under suitable conditions in a liquid or solid medium. In particular embodiments, culturing refers to the fermentative bioconversion of a substrate to an end-product. Culturing media are well known and individual components of such culture media are available from commercial sources, e.g., under the DIFCO™ and BBL™ trademarks. In one non-limiting example, the aqueous nutrient medium is a rich medium comprising complex sources of nitrogen, salts, and carbon, such as YP medium, comprising 10 g/L of peptone and 10 g/L yeast extract of such a medium. The host cell of a culture can be additionally engineered to assimilate carbon efficiently and use cellulosic materials as carbon sources according to methods described in U.S. Pat. Nos. 5,000,000; 5,028,539; 5,424,202; 5,482,846; 5,602,030; WO 2010127318. In addition, in some embodiments the host cell is engineered to express an invertase so that sucrose can be used as a carbon source.

As used herein, the term "under conditions effective to express a genetically engineered polynucleotide sequence" means any condition that allows a host cell to produce desired fatty acid derivatives. Examples are ω-hydroxylated fatty acid and ester derivatives, ω-unsaturated fatty acid and ester derivatives, and 3-hydroxy fatty acid and ester derivatives. Suitable conditions include, for example, fermentation conditions.

The terms "altered level of expression" and "modified level of expression" are used interchangeably and mean that a polynucleotide, polypeptide, metabolite, or product (e.g., fatty acid derivatives, ω-hydroxy fatty acid derivative) is present in a different concentration in an engineered host cell as compared to its concentration in a corresponding wild-type cell under the same conditions.

As used herein, the term "titer" refers to the quantity of fatty acid derivative produced per unit volume of host cell culture. Examples of fatty acid derivatives are ω-fatty acid derivatives and 3-hydroxy fatty acid derivatives. Thus, the titer may refer to a particular (omega) ω-fatty acid derivative or a combination of ω-fatty acid derivatives produced by a given recombinant host cell culture. Similarly, the titer may refer to a particular 3-hydroxy fatty acid derivative or a combination of 3-hydroxy fatty acid derivatives produced by a given recombinant host cell culture.

As used herein, the term "productivity" refers to the quantity of a fatty acid derivative or derivatives produced per unit volume of host cell culture per unit time. Examples of fatty acid derivatives are ω-fatty acid derivatives and 3-hydroxy fatty acid derivatives. The productivity may refer to a particular ω-hydroxylated fatty acid or ester derivative, ω-unsaturated fatty acid or ester derivative, or 3-hydroxy fatty acid or ester derivative or a combinations of such fatty acid derivatives produced by a given recombinant host cell culture.

As used herein, the term "glucose utilization rate" means the amount of glucose used by the culture per unit time, reported as grams/liter/hour (g/L/hr).

The term "carbon-based" when used alone or in reference to a "source" refers to being derived from a carbon source. The carbon source includes any biological material (including renewable feedstocks and/or biomass) from which carbon is derived except oleochemicals (i.e., refined oils from plants and animals such as fatty acids, fatty acid esters, TAGs, hydroxy fatty acids, and the like) and petrochemicals (i.e., chemicals derived from petroleum such as alkanes, alkenes, and the like). Thus, the term "carbon-based", as used herein, excludes carbon derived from oleochemicals and petrochemicals. In one embodiment, the carbon source is a simple carbon source. In some embodiments, the carbon source includes sugars or carbohydrates (e.g., monosaccharides, disaccharides, or polysaccharides). In some embodiments, the carbon source is glucose and/or sucrose. In other embodiments, the carbon source is derived from a renewable feedstock such as carbohydrates from corn, sugar cane, or lignocellulosic biomass; or waste products such as glycerol, flu-gas, syn-gas; or the reformation of organic materials such as biomass or natural gas; or is carbon dioxide that is fixed photosynthetically. In other embodiments, a biomass is processed into a carbon source, which is suitable for bioconversion. In still other embodiments, the biomass does not require further processing into a carbon source but can be used directly as carbon source. An exemplary source of such biomass is plant matter or vegetation, such as switchgrass. Another exemplary carbon source includes metabolic waste products, such as animal matter (e.g., cow manure). Further exemplary sources of carbon include algae and other marine plants. Another carbon source (including biomass) includes waste products from industry, agriculture, forestry, and households, including, but not limited to, fermentation waste, fermentation biomass, glycerol/glycerine, ensilage, straw, lumber, sewage, garbage, maniple solid waste, cellulosic urban waste, and food leftovers.

As used herein, the term "isolated," with respect to products (such as fatty acid derivatives) refers to products that are separated from cellular components, cell culture media, or chemical or synthetic precursors. For example, the ω-hydroxylated fatty acid or ester derivative, ω-unsaturated fatty acid or ester derivative, or 3-hydroxy fatty acid or ester derivative produced by the organisms described herein can be relatively immiscible in the fermentation broth, as well as in the cytoplasm. Therefore, the fatty acid derivatives can collect in an organic phase either intracellularly or extracellularly. In some embodiments, the co fatty acid derivatives collect extracellularly, i.e., are secreted. As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "purify," "purified," or "purification" mean the removal or isolation of a molecule from its environment by, for example, isolation or separation. "Substantially purified" molecules are at least about 60% free (e.g., at least about 70% free, at least about 75% free, at least about 85% free, at least about 90% free, at least about 95% free, at least about 97% free, at least about 99% free) from other components with which they are associated. As used herein, these terms also refer to the removal of contaminants from a sample. For example, the removal of contaminants can result in an increase in the percentage of fatty acid derivatives in a sample. For example, when a fatty acid derivative is produced in a recombinant host cell, the fatty acid derivative can be purified by the removal of host cell proteins. After purification, the percentage of fatty acid derivative in the sample is increased. The terms "purify," "purified," and "purification" are relative terms which do not require absolute purity. Thus, for example, when a fatty acid derivative is produced in recombinant host cells, a purified fatty acid derivative is a fatty acid derivative that is substantially separated from other cellular components (e.g., nucleic acids, polypeptides, lipids, carbohydrates, or other hydrocarbons).

As used herein, the term "non-naturally occurring" when used in reference to a microbial organism or microorganism disclosed herein is intended to mean that the organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes within a fatty acid derivative biosynthetic pathway which include, without limitation, thioesterases, ester synthases, omega hydroxylases, and oxidases or dehydrogenases.

As used herein, the term "CoA" or "coenzyme A" is intended to mean an organic cofactor or prosthetic group (nonprotein portion of an enzyme) whose presence is required for the activity of many enzymes to form an active enzyme system. Coenzyme A functions, for example, in certain condensing enzymes, acts in acetyl or other acyl group transfer and in fatty acid synthesis and oxidation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

As used herein, the term "gene disruption," or grammatical equivalents thereof, is intended to mean a genetic alteration that renders the encoded gene product inactive. The genetic alteration can be, for example, deletion of the entire gene, deletion of a regulatory sequence required for transcription or translation, deletion of a portion of the gene with results in a truncated gene product or by any of various mutation strategies that inactivate the encoded gene product. One particularly useful method of gene disruption is complete gene deletion because it reduces or eliminates the occurrence of genetic reversions in the non-naturally occurring microorganisms of the invention. The term "gene disruption" is also intended to mean a genetic alteration that lowers the activity of a given gene product relative to its activity in a wild-type organism. This attenuation of activity can be due to, for example, a deletion in a portion of the gene which results in a truncated gene product or any of various mutation strategies that render the encoded gene product less active than its natural form, replacement or mutation of the promoter sequence leading to lower or less efficient expression of the gene, culturing the organism under a condition where the gene is less highly expressed than under normal culture conditions, or introducing antisense RNA molecules that interact with complementary mRNA molecules of the gene and alter its expression.

As used herein, the term "eukaryotic organism" refers to any organism having a cell type having specialized organelles in the cytoplasm and a membrane-bound nucleus enclosing genetic material organized into chromosomes. The term is intended to encompass all eukaryotic organisms including eukaryotic microbial organisms such as yeast and fungi. The term also includes cell cultures of any eukaryotic species that can be cultured for the production of a biochemical where the eukaryotic species need not be a microbial organism. A "eukaryotic microbial organism," "eukaryotic microbial organism" or "eukaryotic microorganism" is intended to mean any eukaryotic organism that exists as a microscopic cell that is included within the domain of eukarya.

General Overview The development of a new and environmentally friendly chemo-enzymatic process for the production of chemical compounds that are suitable as fragrance ingredients from microbially-derived fatty acid derivatives denotes a significant improvement to the industry. Particularly, the method provides for the production of these chemical compounds from carbon-based feedstocks such as carbohydrates from corn, cane, or lignocellulosic biomass; waste products such as glycerol, flu-gas, syn-gas; or the reformation of organic materials such as biomass or natural gas or carbon dioxide. This provides a clean and environmentally sustainable process for the production of chemicals such as fragrance ingredients. Since the process allows the compounds to be produced from a simple renewable feedstock there are also distinct economic advantages with respect to cost and operation simplicity.

For example, the chemo-enzymatic process includes a two-step method that produces a fatty acid derivative microbially from a renewable carbon-based feedstock and then synthetically converts the fatty acid derivative into a chemical compound such as a fragrance ingredient. The advantages of this process are that it is a simpler and more cost effective production method, because it employs as a first step a microbial fermentation rather than expensive (and often multiple) chemical and/or biocatalytic processes. Another advantage is that the process is cleaner because fewer waste products are generated. Another advantage is that the process is more sustainable because of the use of renewable feedstock as raw source material, this can even include waste products such as glycerol. Another advantage is the selective manufacture of new specific target products, i.e., novel compositions suitable as fragrances. Still, another advantage is the sudden access to diverse chemical compositions that provide the basis for novel fragrances.

Fragrance ingredients have specific olfactory characteristics and their production has so far been limited by using naturally occurring compounds or petrochemical or oleochemical precursors. The disclosure provides a chemo-enzymatic process that allows for the synthesis of novel chemical structures by using fatty acid derivatives as substrates. In particular, fermentation can alter the position and the configuration of double bonds, introduce methyl branches and vary the carbon chain lengths in fatty acid derivatives. The fatty acid derivatives are then used as precursors for making the fragrance ingredients. This allows for the synthesis of novel chemical structures with potentially more potent or altered olfactory characteristics. To this end, it is well known in the art that the addition of a double bond and/or alteration of its configuration or position has an impact on the volatility of a compound. This can give a compound an intensified or altered fragrance.

One example is globalide (also known as habanolide), which is a metallic smelling, fresh radiant musk. Globalide is a non-natural (i.e., synthetic) mixture of $C_{15}$ cyclic macrolides with one double bond in either the $C_{11}$ or $C_{12}$ position and as cis (z-) or trans (e-) isomers (a mixture of e-11 cyclopentadecenolide, z-11 cyclopentadecenolide, e-12 cyclopentadecenolide and z-12 cyclopentadecenolide). The configuration and position of its double bond is not by design but is determined by the available chemical feedstocks used for its synthesis, cyclododecanone and butadiene. The chemo-enzymatic process allows for the synthesis of isomerically pure habanolides with a double bond in a defined position, for example z-11 cyclopentadecenolide, z-12 cyclopentadecenolide, z-7 cyclopentadecenolide and z-8 cyclopentadecenolide), which are novel compounds with potentially superior olfactory characteristics as compared to synthetic globalide.

Another example is the ambrettolide family. Ambrettolide is a lightly sweetly smelling musk. It naturally occurs in ambrette seeds and it is a $C_{16}$ macrolide with one double bond (z-7 cyclohexadecenolide). Because of the limited supply of the ambrette seeds, it is usually chemically synthesized. However, the natural structure is not accessible through chemical synthesis. The chemical synthesis is limited to its saturated analog, dihydroambrettolide (cyclohexadecanolide), which has inferior olfactory characteristics, or the trans-9 isomer, isoambrettolide (e-9 cyclohexadecenolide). The configuration and position of the double bond of the latter compound is not by design but is determined by the chemical feedstock, which in this case is aleuritic acid. The present chemo-enzymatic process allows for the synthesis of z-9 cyclohexadecenolide, an isoambrettolide with the same double bond configuration as natural ambrettolide, which is a novel compound with potentially superior olfactory characteristics as compared to synthetic isoambrettolide.

Another example is the unsaturated macrocyclic ketone family. Only few macrocyclic ketones are naturally occurring, for example muscone ((−)-(R)-3-methylcyclopentadecanone) from the musk deer or musk rat, and its supply is limited. Macrocyclic ketones are usually chemically synthesized from cyclododecanone by ring extension or by olefinic metathesis. They are usually fully saturated, e.g., romanone (also known as exaltone) (cyclopentadecanone). The present chemo-enzymatic process allows for the synthesis of unsaturated macrocyclic ketones, e.g., cyclopentadecenone or cyclohexadecenone, when an unsaturated dicarboxylic acid, e.g., 1,15 pentadecenedioic acid or 1,16 hexadecenedioic acid, is used as the fatty acid-derivative precursor. These are novel compounds with potentially superior olfactory characteristics as compared to the corresponding synthetic, saturated macrocyclic ketones.

Another example is the gamma or delta lactone (γ- or δ-lactone) family, for example the $C_{12}$ γ-lactone and γ-dodecalactone. Unsaturated γ-lactones are not accessible through chemical synthesis. Biotransformation using expensive oleochemical feedstock such as castor oil or ricinoleic acid allows only for a double bond in the $C_2$ position, e.g., γ-dodec-2-enolactone. The latter process is also difficult to control and γ-dodec-2-enolactone is only a minor fraction of the otherwise saturated dodecalactone. The present chemo-enzymatic process allows for the synthesis of γ-dodec-5-enolactone when an unsaturated 3-hydroxy fatty acid or 3-hydroxy fatty acid ester, e.g., 3-hydroxy dodec-5-enoic acid or 3-hydroxy dodec-5-enoic acid methyl ester, is used as the fatty acid-derivative precursor. The chemo-enzymatic process also allows for the synthesis of methyl-branched γ-lactones, e.g., 9-methyl-γ-dodecalactone, 10-methyl-γ-dodecalactone and 10-methyl-γ-undecalactone, when the corresponding methyl-branched, unsaturated fatty acids or fatty acid esters are used as the fatty acid-derivative precursor. These are novel compounds with potentially superior olfactory characteristics as compared to synthetic or semi-synthetic γ-lactones.

The Microorganisms

The present disclosure provides recombinant microorganisms that have been engineered to convert renewable carbon-based feedstocks, such as carbohydrates, waste products or biomass selectively to specific fatty acid derivatives that serve as microbially-derived precursors for the production of fragrance ingredients. As such, the disclosure contemplates microorganisms that encompass metabolic modifications including altered enzymatic functionalities through engineered microbial fatty acid metabolisms for the conversion of intermediates to specific fatty acid derivatives, e.g., fatty acids and fatty esters that in turn serve as the microbially-derived precursors for the production of fragrance ingredients. The recombinant microorganisms allow for large scale and high-throughput fermentation processes that make the production of fragrance ingredients more cost effective.

Fatty acid synthesis is one of the most conserved systems of the bacterial biosynthetic machinery. The fatty acid synthase (FAS) multi-enzyme complex is present in all bacteria and eukaryotes. Most of the FAS related genes are indispensable for cell growth and survival. Eukaryotic and bacterial FAS drive essentially the same type of biochemical transformation. In eukaryotes, FAS is referred to as FAS I and most of its catalytic domains are encoded by one polypeptide chain (non-dissociable). In prokaryotes such as bacteria, FAS is referred to as FASII and its individual enzymes and carrier proteins are encoded by separate genes coding for discrete (dissociable) proteins.

The acyl carrier protein (ACP) along with the enzymes in a FAS pathway control the length, degree of saturation and branching of the fatty acids produced in a native organism. The steps in this pathway are catalyzed by enzymes of the fatty acid biosynthesis (FAB) and acetyl-CoA carboxylase (ACC) gene families. For example, enzymes that can be included in a FAS pathway include AccABCD, FabD, FabH, FabG, FabA, FabZ, FabI, FabK, FabL, FabM, FabB, and FabF. Depending upon the desired fatty acid derivative product one or more of these genes can be attenuated or over-expressed. As such, microorganisms have been engineered to increase production of fatty acid derivatives from renewable feedstock such as glucose or other carbon sources. Herein the major goal is to increase the activity of key control enzymes that regulate the production of fatty acid derivatives in order to convert the bacterial strain into a microbial factory for fatty acid derivative production, including fatty acids, fatty acid methyl esters (FAMEs), and fatty acid ethyl esters (FAEEs) (see, e.g., U.S. Pat. No. 8,283,143, incorporated herein by reference).

The microorganisms or microbial cells express polynucleotides that encode polypeptides of enzymatic function in order to modify enzymatic pathways for the production of desirable fatty acid derivatives that serve as microbial precursors. These polypeptides, which are identified herein by Enzyme Accession Numbers (EC Numbers), are useful for engineering fatty acid pathways that lead to production of fatty acid derivatives. Table 1 below shows the EC Numbers of enzymes that are useful in the engineering of such fatty acid pathways.

TABLE 1

Enzymatic Activities

| Gene Designation | Source Organism | Enzyme Name | Accession # | EC Number | Exemplary Use |
|---|---|---|---|---|---|
| Fatty Acid Production Increase | | | | | |
| accA | E. coli, Lactococci | Acetyl-CoA carboxylase, subunit A (carboxyltransferase alpha) | AAC73296, NP_414727 | 6.4.1.2 | increase Malonyl-CoA production |
| accB | E. coli, Lactococci | Acetyl-CoA carboxylase, subunit B (BCCP: biotin carboxyl carrier protein) | NP_417721 | 6.4.1.2 | increase Malonyl-CoA production |
| accC | E. coli, Lactococci | Acetyl-CoA carboxylase, subunit C (biotin carboxylase) | NP_417722 | 6.4.1.2, 6.3.4.14 | increase Malonyl-CoA production |
| accD | E. coli, Lactococci | Acetyl-CoA carboxylase, subunit D (carboxyltransferase beta) | NP_416819 | 6.4.1.2 | increase Malonyl-CoA production |
| fadD | E. coli W3110 | acyl-CoA synthase | AP_002424 | 2.3.1.86, 6.2.1.3 | increase Fatty acid production |
| fabA | E. coli K12 | β-hydroxydecanoyl thioester dehydratase/isomerase | NP_415474 | 4.2.1.60 | increase fatty acyl-ACP/CoA production |
| fabB | E. coli | 3-oxoacyl-[acyl-carrier-protein] synthase I | BAA16180 | 2.3.1.41 | increase fatty acyl-ACP/CoA production |
| fabD | E. coli K12 | [acyl-carrier-protein] S-malonyltransferase | AAC74176 | 2.3.1.39 | increase fatty acyl-ACP/CoA production |
| fabF | E. coli K12 | 3-oxoacyl-[acyl-carrier-protein] synthase II | AAC74179 | 2.3.1.179 | increase fatty acyl-ACP/CoA production |
| fabG | E. coli K12 | 3-oxoacyl-[acyl-carrier protein] reductase | AAC74177 | 1.1.1.100 | increase fatty acyl-ACP/CoA production |
| fabH | E. coli K12 | 3-oxoacyl-[acyl-carrier-protein] synthase III | AAC74175 | 2.3.1.180 | increase fatty acyl-ACP/CoA production |
| fabI | E. coli K12 | enoyl-[acyl-carrier-protein] reductase | NP_415804 | 1.3.1.9 | increase fatty acyl-ACP/CoA production |
| fabR | E. coli K12 | Transcriptional Repressor | NP_418398 | none | modulate unsaturated fatty acid production |

TABLE 1-continued

Enzymatic Activities

| Gene Designation | Source Organism | Enzyme Name | Accession # | EC Number | Exemplary Use |
|---|---|---|---|---|---|
| fabV | Vibrio cholerae | enoyl-[acyl-carrier-protein] reductase | YP_001217283 | 1.3.1.9 | increase fatty acyl-ACP/CoA production |
| fabZ | E. coli K12 | (3R)-hydroxymyristol acyl carrier protein dehydratase | NP_414722 | 4.2.1.— | increase fatty acyl-ACP/CoA production |
| fadE | E. coli K13 | acyl-CoA dehydrogenase | AAC73325 | 1.3.99.3, 1.3.99.— | reduce fatty acid degradation |
| fadD | E. coli K12 | acyl-CoA synthetase | NP_416319 | 6.2.1.3 | reduce fatty acid degradation |
| fadA | E. coli K12 | 3-ketoacyl-CoA thiolase | YP_02627 | 2.3.1.16 | reduce fatty acid degradation |
| fadB | E. coli K12 | enoyl-CoA hydratase, 3-OH acyl-CoA epimerase/ dehydrogenase | NP_418288 | 4.2.1.17, 5.1.2.3, 1.1.1.35 | reduce fatty acid degradation |
| fadR | E. coli | transcriptional regulatory protein | NP_415705 | none | Block or reverse fatty acid degradation |
| Chain Length Control | | | | | |
| tesA (with or without leader sequence) | E. coli | thioesterase - leader sequence is amino acids 1-26 | P0ADA1 | 3.1.2.—, 3.1.1.5 | C18 Chain Length |
| tesA (without leader sequence) | E. coli | thioesterase | AAC73596, NP_415027 | 3.1.2.—, 3.1.1.5 | C18:1 Chain Length |
| tesA (mutant of E. coli thioesterase I complexed with octanoic acid) | E. coli | thioesterase | L109P | 3.1.2.—, 3.1.1.5 | <C18 Chain Length |
| fatB1 | Umbellularia californica | thioesterase | Q41635 | 3.1.2.14 | C12:0 Chain Length |
| fatB2 | Cuphea hookeriana | thioesterase | AAC49269 | 3.1.2.14 | C8:0-C10:0 Chain Length |
| fatB3 | Cuphea hookeriana | thioesterase | AAC72881 | 3.1.2.14 | C14:0-C16:0 Chain Length |
| fatB | Cinnamomumcamphora | thioesterase | Q39473 | 3.1.2.14 | C14:0 Chain Length |
| fatB | Arabidopsis thaliana | thioesterase | CAA85388 | 3.1.2.14 | C16:1 Chain Length |
| fatB1 | Umbellularia californica | thioesterase | Q41635 | 3.1.2.14 | C12:0 Chain Length |
| fatA1 | Helianthus annuus | thioesterase | AAL79361 | 3.1.2.14 | C18:1 Chain Length |
| fatA3 | Arabidopsis thaliana | thioesterase | NP_189147, NP_193041 | 3.1.2.14 | C18:1 Chain Length |
| fatA | Brassica juncea | thioesterase | CAC39106 | 3.1.2.14 | C18:1 Chain Length |
| fatA | Cuphea hookeriana | thioesterase | AAC72883 | 3.1.2.14 | C18:1 Chain Length |
| tes | Photbacterium profundum | thioesterase | YP_130990 | 3.1.2.14 | Chain Length |
| tesB | E. coli | thioesterase | NP_414986 | 3.1.2.14 | Chain Length |
| fadM | E. coli | thioesterase | NP_414977 | 3.1.2.14 | Chain Length |
| yciA | E. coli | thioesterase | NP_415769 | 3.1.2.14 | Chain Length |
| ybgC | E. coli | thioesterase | NP_415264 | 3.1.2.14 | Chain Length |
| Saturation Level Control | | | | | |
| Sfa | E. coli | Suppressor of fabA | AAN79592, AAC44390 | none | increase monounsaturated fatty acids |
| fabA | E. coli K12 | β-hydroxydecanoyl thioester dehydratase/isomerase | NP_415474 | 4.2.1.60 | produce unsaturated fatty acids |
| GnsA | E. coli | suppressors of the secG null mutation | ABD18647.1 | none | increase unsaturated fatty acid esters |
| GnsB | E. coli | suppressors of the secG null mutation | AAC74076.1 | none | increase unsaturated fatty acid esters |
| fabB | E. coli | 3-oxoacyl-[acyl-carrier-protein] synthase I | BAA16180 | 2.3.1.41 | modulate unsaturated fatty acid production |
| des | Bacillus subtilis | D5 fatty acyl desaturase | O34653 | 1.14.19 | modulate unsaturated fatty acid production |
| Ester Production | | | | | |
| AT3G51970 | Arabidopsis thaliana | long-chain-alcohol O-fatty-acyltransferase | NP_190765 | 2.3.1.26 | ester production |

TABLE 1-continued

Enzymatic Activities

| Gene Designation | Source Organism | Enzyme Name | Accession # | EC Number | Exemplary Use |
|---|---|---|---|---|---|
| ELO1 | Pichia angusta | Fatty acid elongase | BAD98251 | 2.3.1.— | produce very long chain length fatty acids |
| plsC | Saccharomyces cerevisiae | acyltransferase | AAA16514 | 2.3.1.51 | ester production |
| DAGAT/DGAT | Arabidopsis thaliana | diacylglycerol acyltransferase | AAF19262 | 2.3.1.20 | ester production |
| hWS | Homo sapiens | acyl-CoA wax alcohol acyltransferase | AAX48018 | 2.3.1.20 | ester production |
| aft1 | Acinetobacter sp. ADP1 | bifunctional wax ester synthase/acyl-CoA:diacylglycerol acyltransferase | AAO17391 | 2.3.1.20 | ester production |
| ES9 | Marinobacter hydrocarbonoclasticus | wax ester synthase | ABO21021 | 2.3.1.20 | ester production |
| mWS | Simmondsia chinensis | wax ester synthase | AAD38041 | 2.3.1.— | ester production |
| Fatty Alcohol Output | | | | | |
| | | thioesterases (see above) | | | increase fatty acid/fatty alcohol production |
| BmFAR | Bombyxmori | FAR (fatty alcohol forming acyl-CoA reductase) | BAC79425 | 1.1.1.— | convert acyl-CoA to fatty alcohol |
| acr1 | Acinetobacter sp. ADP1 | acyl-CoA reductase | YP_047869 | 1.2.1.42 | reduce fatty acyl-CoA to fatty aldehydes |
| yqhD | E. coli W3110 | alcohol dehydrogenase | AP_003562 | 1.1.—.— | reduce fatty aldehydes to fatty alcohols; increase fatty alcohol production |
| alrA | Acinetobacter sp. ADP1 | alcohol dehydrogenase | CAG70252 | 1.1.—.— | reduce fatty aldehydes to fatty alcohols |
| BmFAR | Bombyxmori | FAR (fatty alcohol forming acyl-CoA reductase) | BAC79425 | 1.1.1.— | reduce fatty acyl-CoA to fatty alcohol |
| GTNG_1865 | Geobacillusthermodenitrificans NG80-2 | Long-chain aldehyde dehydrogenase | YP_001125970 | 1.2.1.3 | reduce fatty aldehydes to fatty alcohols |
| AAR | Synechococcus elongatus | Acyl-ACP reductase | YP_400611 | 1.2.1.42 | reduce acyl-ACP/CoA to fatty aldehydes |
| carB | Mycobacterium smegmatis | carboxylic acid reductase protein | YP_889972 | 6.2.1.3, 1.2.1.42 | reduce fatty acids to fatty aldehyde |
| FadD | E. coli K12 | acyl-CoA synthetase | NP_416319 | 6.2.1.3 | activates fatty acids to fatty acyl-CoAs |
| atoB | Erwiniacarotovora | acetyl-CoA acetyltransferase | YP_049388 | 2.3.1.9 | production of butanol |
| hbd | Butyrivibriofibrisolvens | Beta-hydroxybutyryl-CoA dehydrogenase | BAD51424 | 1.1.1.157 | production of butanol |
| CPE0095 | Clostridium perfringens | crotonasebutyryl-CoA dehydryogenase | BAB79801 | 4.2.1.55 | production of butanol |
| bcd | Clostridium beijerinckii | butyryl-CoA dehydryogenase | AAM14583 | 1.3.99.2 | production of butanol |
| ALDH | Clostridium beijerinckii | coenzyme A-acylating aldehyde dehydrogenase | AAT66436 | 1.2.1.3 | production of butanol |
| AdhE | E. coli CFT073 | aldehyde-alcohol dehydrogenase | AAN80172 | 1.1.1.1 1.2.1.10 | production of butanol |
| Fatty Alcohol Acetyl Ester Output | | | | | |
| | | thioesterases (see above) | | | modify output |
| acr1 | Acinetobacter sp. ADP1 | acyl-CoA reductase | YP_047869 | 1.2.1.42 | modify output |
| yqhD | E. Coli K12 | alcohol dehydrogenase | AP_003562 | 1.1.—.— | modify output |
| AAT | Fragaria × ananassa | alcohol O-acetyltransferase | AAG13130 | 2.3.1.84 | modify output |
| Terminal Olefin Output | | | | | |
| OleT | Jeotgalicoccus sp. | Fatty acid decarboxylase | HQ709266 | 1.11.2.4 | decarboxylate fatty acids |
| Product Export | | | | | |
| AtMRP5 | Arabidopsis thaliana | Arabidopsis thaliana multidrug resistance-associated | NP_171908 | none | modify product export amount |

TABLE 1-continued

Enzymatic Activities

| Gene Designation | Source Organism | Enzyme Name | Accession # | EC Number | Exemplary Use |
|---|---|---|---|---|---|
| AmiS2 | *Rhodococcus* sp. | ABC transporter AmiS2 | JC5491 | none | modify product export amount |
| AtPGP1 | *Arabidopsis thaliana* | *Arabidopsis thaliana* p glycoprotein 1 | NP_181228 | none | modify product export amount |
| AcrA | *Candidatus-Protochlamydiaamoebophila* UWE25 | putative multidrug-efflux transport protein acrA | CAF23274 | none | modify product export amount |
| AcrB | *Candidatus Protochlamydiaamoebophila* UWE25 | probable multidrug-efflux transport protein, acrB | CAF23275 | none | modify product export amount |
| TolC | *Francisellatularensis* subsp. *novicida* | Outer membrane protein [Cell envelope biogenesis, | ABD59001 | none | modify product export amount |
| AcrE | *Shigella sonnei* Ss046 | transmembrane protein affects septum formation and cell membrane permeability | YP_312213 | none | modify product export amount |
| AcrF | *E. coli* | Acriflavine resistance protein F | P24181 | none | modify product export amount |
| tll1619 | *Thermosynechococcus elongatus* [BP-1] | multidrug efflux transporter | NP_682409.1 | none | modify product export amount |
| tll0139 | *Thermosynechococcus elongatus* [BP-1] | multidrug efflux transporter | NP_680930.1 | none | modify product export amount |
| Fermentation | | | | | |
| replication checkpoint genes | | | | | increase output efficiency |
| umuD | *Shigellasonnei* Ss046 | DNA polymerase V, subunit | YP_310132 | 3.4.21.— | increase output efficiency |
| umuC | *E. coli* | DNA polymerase V, subunit | ABC42261 | 2.7.7.7 | increase output efficiency |
| pntA, pntB | *Shigellaflexneri* | NADH:NADPH transhydrogenase (alpha and beta subunits) | P07001, P0AB70 | 1.6.1.2 | increase output efficiency |
| Other | | | | | |
| fabK | *Streptococcus pneumoniae* | trans-2-enoyl-ACP reductase II | AAF98273 | 1.3.1.9 | Contributes to fatty acid biosynthesis |
| fabL | *Bacillus licheniformis* DSM 13 | enoyl-(acyl carrier protein) reductase | AAU39821 | 1.3.1.9 | Contributes to fatty acid biosynthesis |
| fabM | *Streptococcus mutans* | trans-2, cis-3-decenoyl-ACP isomerase | DAA05501 | 4.2.1.17 | Contributes to fatty acid biosynthesis |

Examples of desirable fatty acid derivatives that will serve as microbial precursors for the chemo-enzymatic process are discussed below. These fatty acid derivatives are produced by the recombinant microorganisms of the present disclosure. The enzymatic functionalities and biochemical pathways discussed below are illustrative examples of how the microorganisms can be manipulated and must not be construed as limiting. One of skill will recognize that there are alternative embodiments of certain enzymatic functionalities that can be combined to achieve the production of fatty acid derivatives.

Odd and Even Chain Fatty Acid Derivatives

*E. coli* cells naturally synthesize even, straight chain fatty acids for membrane biosynthesis. However, recombinant microorganisms (e.g., *E. coli*) can be engineered to produce odd-chain fatty acid derivatives from carbon-based feedstocks. In addition, strains with certain modifications can be combined in order to produce odd straight chain fatty acid derivatives. In one embodiment, recombinant *E. coli* strains that synthesize predominantly odd, straight chain fatty acids from carbon-based feedstocks have the activity of an endogenous acetyl-CoA specific 3-oxoacyl-[acyl-carrier-protein] synthase III (FabH) (EC 2.3.1.180) attenuated and the activity of a 3-oxoacyl-[acyl-carrier-protein] synthase III with broad substrate specificity increased, e.g., FabH1 from *Bacillus subtilis* can be overexpressed. In other embodiments, the modified strains may have an additional modified activity of enzymes of the threonine biosynthesis pathway, e.g., aspartate kinase I/homoserine dehydrogenase I (ThrA), homoserine kinase (ThrB) and threonine synthase (ThrC), and/or a modified activity of enzymes of the leucine biosynthesis pathway, e.g., 3-isopropylmalate dehydrogenase (LeuB), isopropylmalate (IPM) isomerase and isopropylmalate (IPM) isomerase (LeuD), and/or a modified activity of threonine deaminase (IlvA) or threonine dehydratase (TdcB). Such strains may also have a citramalate synthase (CimA) overexpressed, e.g., from Methanococcus jannaschii (see, e.g., U.S. Pat. No. 8,372,610, incorporated herein by reference).

Branched Chain Fatty Acid Derivatives

Recombinant microorganisms (e.g., *E. coli*) can be engineered to produce branched-chain fatty acid derivatives from carbon-based feedstocks. For example, *E. coli* strains that synthesize even and odd chain, methyl-branched fatty acids from carbon-based feedstocks can have modifications in addition to the ones that allow *E. coli* to synthesize odd-chain fatty acids. In one embodiment, such strains overexpress a branched-chain α-ketoacid dehydrogenase enzyme complex (Bkd) and a lipoamide dehydrogenase (lpd), e.g., from *Pseudomonas putida*. In another embodiment, such strains also have a modified activity of enzymes of the isoleucine biosynthesis pathway, e.g., acetohydroxy acid isomeroreductase (IlvC), dihydroxy-acid dehydratase (IlvD) and acetohydroxyacid synthase II (IlvGM) (see, e.g., U.S. Pat. No. 8,530,221, incorporated herein by reference). In other embodiments, the strains express similar Bkd-like and lpd-like enzymatic functionalities and/or combinations thereof to produce branched-chain fatty acid derivatives.

Unsaturated Fatty Acid Derivatives

Most microorganisms (e.g., *E. coli*) naturally synthesize saturated and monounsaturated fatty acids. Recombinant microorganisms (e.g., *E. coli* strains) can be engineered to over- or underproduce unsaturated fatty acid derivatives from carbon-based feedstocks. In one embodiment, the ratio of saturated to monounsaturated saturated fatty acids can be altered by modifying the activity of certain transcriptional regulator proteins, e.g., FadR and FabR, and/or by directly modifying the enzyme activity of (3R)-hydroxymyristoyl acyl carrier protein dehydratase (FabZ) (EC 4.2.1.-), β-hydroxydecanoyl thioester dehydratase/isomerase (FabA) (EC 4.2.1.60) and 3-oxoacyl-[acyl-carrier-protein] synthase I (FabB) (EC 2.3.1.41). In another embodiment, the level of unsaturation can be further increased by overexpression of desaturases (EC 1.14.19). Such strains may synthesize mono- or double-unsaturated fatty acids. In still another embodiment, such strains also overexpress certain ferredoxins and/or ferredoxin reductases. Thus, when strains that have specific modification (supra) are combined, increased or decreased amounts of unsaturated fatty acid derivatives can be produced (see, e.g., PCT International Publication No. WO2013/019647, incorporated herein by reference).

Fatty Acids

Recombinant microorganisms (e.g., *E. coli* strains) can be engineered to overproduce fatty acids from carbon-based feedstocks. In one embodiment, a recombinant microorganism has a modified thioesterase enzyme activity (EC 3.1.2.14). For example, fatty acid production can be increased by either deregulating or modifying certain endogenous thioesterases (e.g., TesA) or by overexpressing exogenous thioesterases (e.g., FatB1 from *Umbellularia california*) (see, e.g., U.S. Patent Application Publication No. 2010/0154293, incorporated herein by reference). In another embodiment, the strain will include a similar (e.g., thioesterase-like) enzymatic functionality in order to produce increased amounts of fatty acids.

Fatty Acid Esters

Recombinant microorganisms (e.g., *E. coli* strains) can be engineered to overproduce fatty acid esters from carbon-based feedstocks. In one embodiment, recombinant microorganisms (e.g., *E. coli* strains) that produce fatty esters such as fatty acid methyl ester (FAME) or fatty acid ethyl ester (FAEE) from carbon-based feedstocks and methanol or ethanol, respectively, overexpress an ester synthase (ES) (EC 2.3.1.20), e.g., from *Marinobacter hydrocarbonoclasticus*. In other embodiments, such strains also have a modified thioesterase enzyme activity (TE) (EC 3.1.2.14) and a modified acyl-CoA synthetase activity (FadD) (EC 6.2.1.3). A modified thioesterase enzyme activity can be achieved by either deregulating or modifying certain endogenous thioesterase genes (e.g., TesA) or overexpressing exogenous thioesterases (e.g., FatB1 from *Umbellularia california* or or FatA3 from *Arabidopsis thaliana*) (see, e.g., U.S. Patent Application Publication Nos. 2010/0242345 and 2011/0072714, incorporated herein by reference). In yet another embodiment, the strains have a modified thioesterase enzyme activity and a modified ester synthase activity by engineering a microorganism to overexpress a single enzyme such as a thioesterase capable of producing increased amounts of both fatty acids and fatty esters (see, e.g., U.S. Patent Application Publication No. 2010/0154293, incorporated herein by reference).

3-Hydroxy Fatty Acids

Recombinant microorganisms (e.g., *E. coli* strains) can produce 3-hydroxy fatty acids from carbon-based feedstocks. In one embodiment, recombinant microorganisms that produce 3-hydroxy fatty acids have a modified thioesterase enzyme activity (EC 3.1.2.14). This modified enzymatic activity can be achieved by either deregulating or modifying certain endogenous thioesterase genes (e.g., TesB), or overexpressing exogenous thioesterases (e.g., FatB1 from *Umbellularia california* or PhaG from *Pseudomoans putida*). In another embodiment, the strain will include another (e.g., thioesterase-like) enzymatic functionality in order to produce increased amounts of 3-hydroxy fatty acids.

3-Hydroxy Fatty Acid Esters

Recombinant microorganisms (e.g., *E. coli* strains) can produce 3-hydroxy fatty acid esters from carbon-based feedstocks. In one embodiment, recombinant *E. coli* strains that produce 3-hydroxy fatty esters such as 3-hydroxy fatty acid methyl ester (3-OH FAME) or 3-hydroxy fatty acid ethyl ester (3-OH FAEE) from carbon-based feedstocks and methanol or ethanol, respectively, overexpress an ester synthase (ES) (EC 2.3.1.20), e.g., from *Marinobacter hydrocarbonoclasticus*. Such strains may also have modified thioesterase activity (TE) (EC 3.1.2.14) and modified acyl-CoA synthetase activity (FadD) (EC 6.2.1.3). A modified thioesterase enzyme activity can be achieved by either deregulating or modifying certain endogenous thioesterase genes (e.g., TesB) or overexpressing exogenous thioesterases (e.g., FatB1 from *Umbellularia california* or PhaG from *Pseudomoans putida*). In another embodiment, the strain will include other (e.g., thioesterase-like and/or ester synthase-like) enzymatic functionalities in order to produce increased amounts of 3-hydroxy fatty esters.

ω-Hydroxy Fatty Acids

Recombinant microorganisms (e.g., *E. coli* strains) can produce ω-hydroxy fatty acids from carbon-based feedstocks. In one embodiment, recombinant *E. coli* strains that produce ω-hydroxy fatty acids have a modified thioesterase enzyme activity (EC 3.1.2.14) and overexpress an ω-hydroxylase/ω-oxygenase, (EC 1.14.15.3) (see Table 2A-2C below), e.g., a self-sufficient hybrid (chimeric) cyp153A oxygenase. A modified thioesterase enzyme activity can be achieved by either deregulating or modifying certain endogenous thioesterase genes (e.g., TesA) or overexpressing exogenous thioesterases (e.g., FatB1 from *Umbellularia california* or FatA3 from *Arabidopsis thaliana*). In other embodiments, the strain will include other enzymatic functionalities (e.g., thioesterase-like and/or ω-hydroxylase/ω-oxygenase-like) in order to produce increased amounts of ω-hydroxy fatty acids (see, e.g., PCT International Publication No. WO2014/201474 A1, incorporated herein by reference).

ω-Hydroxy Fatty Acid Esters

Recombinant microorganisms (e.g., *E. coli* strains) can produce ω-hydroxy fatty acid esters from carbon-based feedstocks. In one embodiment, recombinant *E. coli* strains that produce ω-hydroxy fatty esters such as ω-hydroxy fatty acid methyl ester (ω-OH FAME) or ω-hydroxy fatty acid ethyl ester (ω-OH FAEE) from carbon-based feedstocks and methanol or ethanol, respectively, overexpress an ester synthase (ES) (EC 2.3.1.20), e.g., from *Marinobacter hydrocarbonoclasticus*, and an ω-hydroxylase/ω-oxygenase, (EC 1.14.15.3) (see Table 2A-2C below), e.g., a self-sufficient hybrid (chimeric) cyp153A oxygenase. Such strains may also have a modified thioesterase activity (TE) (EC 3.1.2.14) and a modified acyl-CoA synthetase activity (FadD) (EC 6.2.1.3). A modified thioesterase enzyme activity can be achieved by either deregulating or modifying certain endogenous thioesterase genes (e.g., TesA) or overexpressing exogenous thioesterases (e.g., FatB1 from *Umbellularia california* or FatA3 from *Arabidopsis thaliana*). In other embodiments, the strain will include other (e.g., thioesterase-like and/or ester synthase-like and/or ω-hydroxylase/ω-oxygenase-like) enzymatic functionalities in order to produce increased amounts of ω-hydroxy fatty acids (see, e.g., PCT International Publication No. WO2014/201474 A1, supra).

α,ω-Dicarboxylic Acids

Recombinant microorganisms (e.g., *E. coli* strains) can produce α,ω-dicarboxylic acids from carbon-based feedstocks. In one embodiment, recombinant *E. coli* strains that produce α,ω-dicarboxylic acids have a modified thioesterase enzyme activity (EC 3.1.2.14) and overexpress a ω-hydroxylase/ω-oxygenase, (EC 1.14.15.3) (see Table 2A-2C below), e.g., a self-sufficient hybrid (chimeric) cyp153A oxygenase. In another embodiment, such strains encompass additional oxidases or dehydrogenases, e.g., alcohol oxidase, alkJ, and aldehyde dehydrogenase, alkH, from *Pseudomonas putida* (see Table 3A-3B below) or modified or overexpressed versions thereof. A modified thioesterase enzyme activity can be achieved by either deregulating or modifying certain endogenous thioesterase genes (e.g., TesA) or overexpressing exogenous thioesterases (e.g., FatB1 from *Umbellularia california* or FatA3 from *Arabidopsis thaliana*). In other embodiments, the strain will include other (e.g., thioesterase-like and/or ω-hydroxylase/ω-oxygenase-like and/or dehydrogenase-like and/or oxidase-like) enzymatic functionalities in order to produce increased amounts of α,ω-dicarboxylic acids (see, e.g., PCT International Publication No. WO2014/201474 A1, supra).

α,ω-Dicarboxylic Esters

Recombinant microorganisms (e.g., *E. coli* strains) can produce α,ω-dicarboxylic esters from carbon-based feedstocks. In one embodiment, recombinant *E. coli* strains that produce am-dicarboxylic esters such as ω-hydroxy fatty acid methyl ester (ω-OH FAME) or ω-hydroxy fatty acid ethyl ester (ω-OH FAEE) from carbon-based feedstocks and methanol or ethanol, respectively, overexpress an ester synthase (ES) (EC 2.3.1.20), e.g., from *Marinobacter hydrocarbonoclasticus*, and a ω-hydroxylase/ω-oxygenase, (EC 1.14.15.3) (see Table 2A-2C below), e.g., a self-sufficient hybrid (chimeric) cyp153A oxygenase, and additional oxidases or dehydrogenases, e.g., alcohol oxidase, alkJ, and aldehyde dehydrogenase, alkH, from *Pseudomonas putida* (see Table 3A-3B below). In another embodiment, such strains also have modified thioesterase activity (TE) (EC 3.1.2.14) and modified acyl-CoA synthetase activity (FadD) (EC 6.2.1.3). A modified thioesterase enzyme activity can be achieved by either deregulating or modifying certain endogenous thioesterase genes (e.g., TesA) or overexpressing exogenous thioesterases (e.g., FatB1 from *Umbellularia california* or FatA3 from *Arabidopsis thaliana*). In other embodiments, the strain will include other (e.g., thioesterase-like and or ester synthase-like and/or ω-hydroxylase/ω-oxygenase-like and/or dehydrogenase-like and/or oxidase-like) enzymatic functionalities in order to produce increased amounts of α,ω-dicarboxylic esters (see, e.g., PCT International Publication No. WO2014/201474 A1, supra).

TABLE 2A

Examples of ω-Hydroxylase/ω-Oxygenase (EC 1.14.15.3)

| Gene Designation | Source Organism | Accession No. | Redox System | Hydroxylation Position |
|---|---|---|---|---|
| cyp153A (aciA) | *Acinetobacter* sp. OC4 | BAE78452 | operon with ferredoxin and ferredoxin reductase | ω-hydroxylase |
| cyp153A16 | *Mycobacterium marinum* M | YP_001851443 | operon with ferredoxin and ferredoxin reductase | ω-hydroxylase |
| cyp153A6 | *Mycobacterium* sp. HXN-1500 | AJ833989 | operon with ferredoxin and ferredoxin reductase | ω-hydroxylase |
| cyp153A | *Marinobacter aquaeolei* VT8 | YP_957888 | operon with ferredoxin and ferredoxin reductase | ω-hydroxylase |
| alkB | *Pseudomonas putida* GPo1 | CAB54050 | requires rubredoxin and rubredoxin reductase | ω-hydroxylase |
| alkB | *Pseudomonas fluorescens* CHA0 | CAB51045 | requires rubredoxin and rubredoxin reductase | ω-hydroxylase |
| alkM | *Acinetobacter baylyi* | YP_046098 | requires rubredoxin and rubredoxin reductase | ω-hydroxylase |
| alkB | *Gordonia* sp. SoGc | ADT82701 | requires rubredoxin and rubredoxin reductase | ω-hydroxylase |
| alkW1 | *Dietzia* sp. DQ12-45-1b | HQ850582 | c-terminal rubredoxin fusion, requires rubredoxin reductase | ω-hydroxylase |
| alkB | *Pseudomonas putida* GPo1 | CAB54050 | requires rubredoxin and rubredoxin reductase | ω-hydroxylase |
| alkB | *Pseudomonas fluorescens* CHA0 | CAB51045 | requires rubredoxin and rubredoxin reductase | ω-hydroxylase |

TABLE 2B

Examples of Redox Partners for ω-Hydroxylase/ω-Oxygenase (EC 1.14.15.3)

| Designation/Name | Organism | Accession # |
|---|---|---|
| ferredoxin, ferredoxin reductase | *Acinetobacter* sp. OC4 | BAE78451, BAE78453 |
| ferredoxin, ferredoxin reductase | *Mycobacterium marinum* M | YP_001851444, YP_001851442 |
| ferredoxin, ferredoxin reductase | *Marinobacter aquaeoli* VT8 | YP_957887, YP_957889 |
| alkG, alkT | *Pseudomonas putida* GPo1 | CAB54052, CAB54063 |
| rubA, rub | *Acinetobacter baylyi* ADP1 | CAA86925, CAA86926 |

TABLE 2C

Examples of Self-Sufficient ω-1, ω-2, ω-3-Hydroxylase/Oxygenase (EC 1.14.14.1) Fusion Proteins

| Gene Designation | Source Organism | Accession No. | Redox System | Hydroxylation Position |
|---|---|---|---|---|
| P450-BM3 (cyp102A1) | *Bacillus megaterium* | AAA87602 | fusion protein with reductase domain | ω-1,-2,-3 hydroxylation |
| yrhJ (cyp102A3) | *Bacillus subtilis* | NP_390594 | fusion protein with reductase domain | ω-1,-2,-3 hydroxylation |
| yrhJ (cyp102A7) | *Bacillus licheniformis* | AAU41718 | fusion protein with reductase domain | ω-1,-2,-3 hydroxylation |

TABLE 3A

Examples of Alcohol Dehydrogenase (EC 1.1.1.1/2) or Alcohol Oxidase (EC 1.1.3.13, EC 1.1.3.20)

| Designation/Name | Organism | Accession # |
|---|---|---|
| alkJ | *Pseudomonas putida* GPo1 | CAB54054 |
| alkJ | *Alcanivorax borkumensis* AP1 | CAC38030 |
| cddC | *Rhodococcus ruber* SC1 | AAL14237 |

TABLE 3B

Examples of Aldehyde Dehydrogenase (EC 1.2.1.3/4/5/) or Aldehyde Oxidase (EC 1.2.3.1)

| Designation/Name | Organism | Accession # |
|---|---|---|
| alkH | *Pseudomonas putida* GPo1 | CAB51050 |
| alkH | *Alcanivorax borkumensis* AP1 | CAC38029 |
| cddD | *Rhodococcus ruber* SC1 | AAL14238 |

Metabolic Modifications via Altered Enzymatic Functionalities

FadR (see Table 1, supra) is a key regulatory factor involved in fatty acid degradation and fatty acid biosynthetic pathways (Cronan et al. (1998) *Mol. Microbiol.*, 29(4): 937-943). The *E. coli* enzyme FadD (see Table 1, supra) and the fatty acid transport protein FadL are components of a fatty acid uptake system. FadL mediates transport of fatty acids into the bacterial cell, and FadD mediates formation of acyl-CoA esters. When no other carbon source is available, exogenous fatty acids are taken up by bacteria and converted to acyl-CoA esters, which can bind to the transcription factor FadR and depress the expression of the fad genes that encode proteins responsible for fatty acid transport (FadL), activation (FadD), and β-oxidation (FadA, FadB, and FadE,). When alternative sources of carbon are available, bacteria synthesize fatty acids as acyl-ACPs, which are used for phospholipid synthesis, but are not substrates for β-oxidation. Thus, acyl-CoA and acyl-ACP are both independent sources of fatty acids that can result in different end-products (Caviglia et al. (2004) *J. Biol. Chem.*, 279(12): 1163-1169).

In one illustrative embodiment, pathways use a renewable feedstock such as glucose to produce ω-hydroxy fatty acid derivatives. Glucose is converted to an acyl-ACP by the native organism. Polynucleotides that code for polypeptides with fatty acid degradation enzyme activity can be optionally attenuated depending on the desired product. Non-limiting examples of such polypeptides are acyl-CoA synthetase (FadD) and acyl-CoA dehydrogenase (FadE). Table 1 provides a comprehensive list of enzymatic activity (supra) within the metabolic pathway, including various fatty acid degradation enzymes that can be optionally attenuated according to methods known in the art.

In another illustrative embodiment, pathways use a renewable feedstock such as glucose to produce α,ω-diacids. In one particular embodiment, an acyl-ACP can be converted to an α,ω-diacid via two similar pathways, employing a $C_{12}$ free fatty acid as a precursor intermediate or a $C_{12}$ fatty acid methyl ester (FAME) as an intermediate.

Another illustrative embodiment contemplates the production of various chemical compounds, including ω-hydroxy fatty acids, ω-oxo fatty acids, and α,ω-diacids. In order to do this, a thioesterase is employed to covert an acyl-ACP to a free fatty acid. Herein, the gene encoding the thioesterase can be tesA, 'tesA, tesB, fatB1, fatB2, fatB3, fatAl, or fatA (see also Table 1, supra). An ω-hydroxylase also known as ω-oxygenase can be used to generate ω-hydroxy fatty acids. Examples for suitable ω-hydroxylases/ω-oxygenases (EC 1.14.15.3) and their redox partners are listed in Tables 2A and 2B (supra). These are certain non-heme di-iron oxygenases (e.g., alkB from *Pseudomonas putida* GPo1) or certain heme-type P450 oxygenases (e.g., cyp153A from *Marinobacter aquaeolei*) also known as cytochrome P450s. Cytochromes P450s are ubiquitously distributed enzymes, which possess high complexity and display a broad field of activity. They are hemoproteins encoded by a superfamily of genes converting a broad variety of substrates and catalyzing a variety of interesting chemical reactions. Cyp153A is a family of soluble bacterial cytochrome P450s that hydroxylate hydrocarbon chains with high selectivity for the ω-position (van Beilen et al. (2006) *Appl. Environ. Microbiol.* 72:59-65). Members of the cyp153A family have been shown in vitro to selectively hydroxylate the ω-position of alkanes, fatty acids or fatty alcohols, for example cyp153A6 from *Mycobacterium* sp.

HXN-1500 (Funhoff et al. (2006) *J. Bacteriol.* 188:5220-5227), cyp153A16 from *Mycobacterium marinum* and cyp153A from *Polaromonas* sp. JS666 (Scheps et al. (2011) *Org. Biomol. Chem.* 9:6727-6733) or cyp153A from *Marinobacter aquaeoli* (Honda-Malca et al. (2012) *Chem. Commun.* 48:5115-5117).

Thus, the present disclosure provides microorganisms that can efficiently and selectively produce ω-hydroxy fatty acid derivatives including am-bifunctional fatty acid derivatives in vivo. The route to α,ω-diacids through a ω-hydroxy fatty acid methyl ester, or a route to α,ω-diacids through a am-fatty acid dimethyl ester can be advantageous, because the methyl esters are not charged which provides advantages for large scale production and recovery. In addition, an alcohol dehydrogenase or oxidase can further convert the ω-hydroxy fatty acid to an ω-oxo fatty acid (Table 3A, supra, shows polypeptides that have the enzymatic activity of an alcohol dehydrogenase or oxidase that can be used to catalyze this step). For example, suitable enzymes that can oxidize 12-hydroxy dodecanoic acid or 12-hydroxy dodecanoic acid methyl ester to 12-oxo dodecanoic acid or 12-oxo dodecanoic acid methyl ester are alcohol oxidases (flavoproteins, e.g., alkJ from *Pseudomonas putida*) (EC 1.1.3.13, EC 1.1.3.20) or NAD(P)-dependent alcohol dehydrogenases (e.g., cddC from *Rhodococcus ruber* (EC 1.1.1.1) (see Table 3A, supra).

Recombinant Microorganisms and Fermentation

In order to produce fatty acid derivatives via a host cell, a number of modifications can be made to production host cells or microrganisms (supra). Thus, the disclosure provides recombinant host cells which have been engineered to provide fatty acid biosynthesis pathways relative to non-engineered or native host cells (e.g., wild type host cells that function as control cells), which is accomplished, for example, through specific strain improvements. Microorganisms such as bacteria, cyanobacteria, yeast, algae, or filamentous fungi can be used as production hosts. Non-limiting examples of microorganisms that may be used as production hosts include *E. coli, S. cerevisiae*, and others (infra).

Microbial strains efficiently convert glucose or other renewable feedstock into fatty acids or fatty acid esters, such as fatty acid methyl esters (FAMEs), fatty acid ethyl esters (FAEEs), and other fatty acid derivatives (supra). In order to achieve that, the strains are carefully engineered to express key enzymes including thioesterases (e.g., TesA from *E. coli*) for the production of fatty acids, or ester synthases (e.g., ES9 from *M. hydrocarbonoclasticus*) for the production of FAME or FAEE. Protocols and procedures for high density fermentations for the production of various compounds have been established (see U.S. Pat. Nos. 8,372,610; 8,323,924; 8,313,934; 8,283,143; 8,268,599; 8,183,028; 8,110,670; 8,110,093; and 8,097,439, all of which are incorporated herein by reference).

By using genetic engineering techniques, the enzymatic steps discussed herein can be added to microbial host cells that may function as biocatalysts. In one embodiment, the fermentation products are secreted outside of the cells, allowing for easy conversion to fragrance ingredients via synthetic methods. Certain recombinant enzymatic steps can be combined in a microbial cell for the direct production of specific fatty acid derivatives. Notably, methods to directly and efficiently produce ω-hydroxy fatty acid derivatives such as, for example, bifunctionals including α,ω-diacids from glucose or other renewable feedstocks other than exogenous fatty acids or paraffins did not exist until now. These bifunctional fatty acid derivatives are suitable precursors for creating fragrance ingredients. The fermentation based method for the production of fatty acid derivatives, including ω-hydroxy fatty acid derivatives provides a fast and environmentally friendly alternative to chemical methods employed in the art.

The present method provides for the direct production of fatty acid derivatives from renewable biomass derived materials (i.e., renewable feedstocks), such as carbohydrates from corn, cane, or lignocellulosic biomass; or waste products such as glycerol, flu-gas, syn-gas; or the reformation of organic materials such as biomass or natural gas or carbon dioxide. In that, the method provides alternative renewable sources for the production of these important intermediates. Since the method allows the compounds to be produced directly and selectively from a simple renewable feedstock there are definite advantages from the perspective of cost and environmental safety. The method includes producing fatty acid derivatives by providing a recombinant microorganism (e.g., host cell) in a fermentation broth; adding a renewable feedstock to a fermentation broth; and optionally isolating the fatty acid derivative from the fermentation broth in order to convert them synthetically to chemicals such as lactones and/or macrocyclic ketones, which provide the building blocks for fragrance ingredients. In one illustrative embodiment, the host cell of a particular microorganism includes a pathway that was engineered to express at least two nucleic acid sequences encoding a polypeptide including a thioesterase or an ester synthase and an ω-hydroxylase.

In some embodiments, the host cell is cultured in a culture medium comprising an initial concentration of a carbon source such as a renewable feedstock of about 2 g/L to about 100 g/L. In other embodiments, the culture medium comprises an initial concentration of about 2 g/L to about 10 g/L of a carbon source, of about 10 g/L to about 20 g/L of a carbon source, of about 20 g/L to about 30 g/L of a carbon source, of about 30 g/L to about 40 g/L of a carbon source, or of about 40 g/L to about 50 g/L of a carbon source. In some embodiments, the fermentation may be monitored for the level of carbon source in the culture medium. In some embodiments, the method further includes adding a supplemental carbon source to the culture medium when the level of the carbon source in the medium is less than about 0.5 g/L. In some embodiments, supplemental carbon source is added to the culture medium when the level of the carbon source in the medium is less than about 0.4 g/L, less than about 0.3 g/L, less than about 0.2 g/L, or less than about 0.1 g/L. In some embodiments, the supplemental carbon source is added to maintain a carbon source level of about 1 g/L to about 25 g/L. In some embodiments, the supplemental carbon source is added to maintain a carbon source level of about 2 g/L or more (e.g., about 2 g/L or more, about 3 g/L or more, about 4 g/L or more). In certain embodiments, the supplemental carbon source is added to maintain a carbon source level of about 5 g/L or less (e.g., about 5 g/L or less, about 4 g/L or less, about 3 g/L or less). In some embodiments, the supplemental carbon source is added to maintain a carbon source level of about 2 g/L to about 5 g/L, of about 5 g/L to about 10 g/L, or of about 10 g/L to about 25 g/L. In some embodiments, the carbon source is glucose or another type of renewable feedstock such as glycerol.

In some embodiments, the fatty acid derivative is produced at a concentration of about 1 g/L to about 200 g/L. In some embodiments, the fatty acid derivative is produced at a concentration of about 1 g/L or more (e.g., about 1 g/L or more, about 10 g/L or more, about 20 g/L or more, about 50 g/L or more, about 100 g/L or more). In some embodiments, the fatty acid derivative is produced at a concentration of about 1 g/L to about 170 g/L, of about 1 g/L to about 10 g/L, of about 40 g/L to about 170 g/L, of about 100 g/L to about 170 g/L, of about 10 g/L to about 100 g/L, of about 1 g/L to about 40 g/L, of about 40 g/L to about 100 g/L, or of about 1 g/L to about 100 g/L.

In some embodiments, the fatty acid derivative is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, an ω-fatty acid derivative is produced at a titer of more than 100 g/L, more than 200 g/L, more than 300 g/L, or higher, such as 500 g/L, 700 g/L, 1000 g/L, 1200 g/L, 1500 g/L, or 2000 g/L. The preferred titer of fatty acid derivative produced by a recombinant host cell according to the methods of the disclosure is from 5 g/L to 200 g/L, 10 g/L to 150 g/L, 20 g/L to 120 g/L and 30 g/L to 100 g/L. In one embodiment, the titer of ω-fatty acid derivative produced by a recombinant host cell according to the methods of the disclosure is about 1 g/L to about 250 g/L and more particularly, 90 g/L to about 120 g/L. The titer may refer to a particular fatty acid derivative or a combination of fatty acid derivatives produced by a given recombinant host cell culture.

In other embodiments, the host cells engineered to produce fatty acid derivatives according to the methods of the disclosure have a yield of at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30%, or at least 40% or a range bounded by any two of the foregoing values. In other embodiments, a fatty acid derivative or derivatives is produced at a yield of more than 30%, 40%, 50%, 60%, 70%, 80%, 90% or more. Alternatively, or in addition, the yield is about 30% or less, about 27% or less, about 25% or less, or about 22% or less. Thus, the yield can be bounded by any two of the above endpoints. For example, the yield of a fatty acid derivative or derivatives produced by the recombinant host cell according to the methods of the disclosure can be 5% to 15%, 10% to 25%, 10% to 22%, 15% to 27%, 18% to 22%, 20% to 28%, or 20% to 30%. In a particular embodiment, the yield of a fatty acid derivative or derivatives produced by the recombinant host cell is about 10% to about 40%. In another particular embodiment, the yield of a fatty acid derivative or derivatives produced by the recombinant host cell is about 25% to about 30%. The yield may refer to a particular fatty acid derivative or a combination of fatty acid derivatives produced by a given recombinant host cell culture. In addition, the yield will also be dependent on the feedstock used.

In some embodiments, the productivity of an fatty acid derivative or derivatives produced by a recombinant host cell is at least 100 mg/L/hour, at least 200 mg/L/hour, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, or at least 2500 mg/L/hour. For example, the productivity of a fatty acid derivative or derivatives produced by a recombinant host cell according to the methods of the disclosure may be from 500 mg/L/hour to 2500 mg/L/hour, or from 700 mg/L/hour to 2000 mg/L/hour. In one embodiment, the productivity is about 0.7 mg/L/h to about 3 g/L/h. The productivity may refer to a particular fatty acid derivative or a combination of fatty acid derivatives produced by a given recombinant host cell culture.

In some embodiments, the host cell is selected from a bacterial cell, yeast cell, fungus cell, and/or filamentous fungi cell. In particular embodiments, the host cell is selected from the genus *Escherichia*, *Bacillus*, *Lactobacillus*, *Rhodococcus*, *Synechococcus*, *Synechoystis*, *Pseudomonas*, *Aspergillus*, *Trichoderma*, *Neurospora*, *Fusarium*, *Humicola*, *Rhizomucor*, *Kluyveromyces*, *Pichia*, *Mucor*, *Myceliophtora*, *Penicillium*, *Phanerochaete*, *Pleurotus*, *Trametes*, *Chrysosporium*, *Saccharomyces*, *Stenotrophamonas*, *Schizosaccharomyces*, *Yarrowia*, or *Streptomyces*.

In other embodiments, the host cell is a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell. In certain embodiments, the host cell is a *Synechococcus* sp. PCC7002, *Synechococcus elongatus* PCC 7942, *Synechoystis* sp. PCC 6803, *Synechococcus elongatus* PCC6301, *Prochlorococcus marinus* CCMP1986 (MED4), *Anabaena variabilis* ATCC29413, *Nostoc punctiforme* ATCC29133 (PCC73102), *Gloeobacter violaceus* ATCC29082 (PCC7421), *Nostoc* sp. ATCC27893 (PCC7120), *Cyanothece* sp. PCC7425 (29141), *Cyanothece* sp. ATCC51442, or *Synechococcus* sp. ATCC27264 (PCC7002). In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor michei* cell. In other embodiments, the host cell is an Actinomycetes cell. In yet other embodiments, the host cell is a *Streptomyces lividans* cell or a *Streptomyces murinus* cell. In other embodiments, the host cell is a *Saccharomyces cerevisiae* cell.

In yet other embodiments, the host cell is a cell from an eukaryotic plant, algae, cyanobacterium, green-sulfur bacterium, green non-sulfur bacterium, purple sulfur bacterium, purple non-sulfur bacterium, extremophile, yeast, fungus, engineered organisms thereof, or a synthetic organism. In certain embodiments, the host cell is a cell from *Arabidopsis thaliana, Panicum virgatums, Miscanthus giganteus, Zea mays, botryococcuse braunii, Chalamydomonas reinhardtii, Dunaliela salina, Thermosynechococcus elongatus, Chlorobium tepidum, Chloroflexus auranticus, Chromatiumm vinosum, Rhodospirillum rubrum, Rhodobacter capsulatus, Rhodopseudomonas palusris, Clostridium ljungdahlii, Clostridiuthermocellum*, or *Pencillium chrysogenum*. In certain other embodiments, the host cell is from *Pichia pastories, Saccharomyces cerevisiae, Yarrowia lipolytica, Schizosaccharomyces pombe, Pseudomonas fluorescens, Pseudomonas putida* or *Zymomonas mobilis*. In yet further embodiments, the host cell is a cell from *Synechococcus* sp. PCC 7002, *Synechococcus* sp. PCC 7942, or *Synechocystis* sp. PCC6803. In some embodiments, the host cell is a CHO cell, a COS cell, a VERO cell, a BHK cell, a HeLa cell, a Cv1 cell, an MDCK cell, a 293 cell, a 3T3 cell, or a PC12 cell. In particular embodiments, the host cell is an *E. coli* cell. In some embodiments, the *E. coli* cell is a strain B, a strain C, a strain K, or a strain W *E. coli* cell.

The non-naturally occurring microbial host cells or microorganisms may contain stable genetic alterations. These microorganisms can be cultured for greater than five generations without loss of the alteration. Generally, stable genetic alterations include modifications that persist greater than 10 generations, particularly stable modifications will persist more than about 25 generations or greater than 50 generations, including indefinitely.

Those skilled in the art will understand that the genetic alterations, including metabolic modifications exemplified herein may be described with respect to a reference organism, such as *E. Coli* and its corresponding metabolic reactions. However, given the complete genome sequencing of a wide variety of organisms and the high level of skill in the area of genomics, those skilled in the art will readily be able to apply the teachings and guidance provided herein to many other organisms. For example, the metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

In some embodiments, there are provided chemoenzymatic processes for preparing one or more lactone product (e.g., gamma or delta lactone), one or more macrolactone product, or one or more macrocyclic ketone product, or the like. These processes include (i) culturing a non-naturally occurring microbial organism including a set of metabolic modifications for fatty acid derivative production, the set of metabolic modifications including one or more of (a) a thioesterase, (b) an omega hydroxylase, and (c) an ester synthase, the microbial organism providing one or more fatty acid derivatives, wherein the culturing step is performed in a carbon-based feedstock, wherein the at least one type of fatty acid derivative includes a fatty acid functionalized by hydroxylation, unsaturation, esterification, or combinations thereof, and (ii) contacting ex vivo the fatty acid derivatives with a non-enzymatic reagent under conditions sufficient to produce a lactone, a macrolactone, or a macrocyclic ketone product. In some embodiments, the methods disclosed herein further include isolating the fatty acid derivatives prior to the contacting step. In some embodiments, the products are secreted and the fatty acid derivatives can be isolated by any combination of centrifugation, decantation, extraction, filtration, and the like. In some embodiments, the fatty acid derivatives are secreted from the cell and the contacting step is performed without isolating the fatty acid derivatives from the culturing step.

Chemical Transformations

I. Starting Materials and Precursors

Utilizing the aforementioned organisms provides access to numerous biosynthetic materials in the form of fatty acid derivatives. The fatty acid derivatives are used as precursors for subsequent synthetic organic transformations to valuable commodity compounds. In some embodiments, the fatty acid derivative includes, but is not limited to, an unsaturated fatty acid, an unsaturated fatty acid ester, an ω-hydroxy fatty acid, an ω-hydroxy unsaturated fatty acid, an ω-hydroxy fatty acid ester, an ω-hydroxy unsaturated fatty acid ester, a 3-hydroxy fatty acid, a 3-hydroxy unsaturated fatty acid, a 3-hydroxy fatty acid ester, a 3-hydroxy unsaturated fatty acid ester, and combinations thereof.

In some embodiments, fatty acid derivatives that are unsaturated are monounsaturated. For example, unsaturated fatty acid esters may be monounsaturated. In some such embodiments, the unsaturated fatty acid esters may be unsaturated fatty acid methyl esters (FAME) and unsaturated fatty acid ethyl esters (FAEE). Thus, there may be provided unsaturated FAME or unsaturated FAEE that are monounsaturated. In some embodiments, there may be provided access to unsaturated fatty acid esters that are selected from unsaturated FAME, and unsaturated FAEE. In some embodiments, there may be provided biosynthetic access to ω-hydroxy unsaturated fatty acids that are monounsaturated.

In some embodiments, there may be provided access to 3-hydroxy fatty acid esters that are 3-hydroxy fatty acid methyl esters (3-OH FAME) or 3-hydroxy fatty acid ethyl esters (3-OH FAEE). In some embodiments ω-hydroxy fatty acid esters may be omega-hydroxy fatty acid methyl esters (ω-OH FAME) or omega-hydroxy fatty acid ethyl esters (ω-OH FAEE). In some embodiments, the omega-hydroxy unsaturated fatty acid esters may be monounsaturated. In some embodiments, monounsaturated omega-hydroxy fatty acid esters may include, but are not limited to, ω-hydroxy monounsaturated fatty acid methyl esters (ω-OH monounsaturated FAME) and ω-hydroxy monounsaturated fatty acid ethyl esters (ω-OH monounsaturated FAEE). In some embodiments, a 3-hydroxy unsaturated fatty acid may also be monounsaturated. In some embodiments, a 3-hydroxy fatty acid ester may be a 3-hydroxy fatty acid methyl ester (3-OH FAME) or a 3-hydroxy fatty acid ethyl ester (3-OH FAEE). In some embodiments, a 3-hydroxy unsaturated fatty acid ester may be monounsaturated. In some embodiments, the monounsaturated 3-hydroxy fatty acid ester may be a monounsaturated 3-OH FAME or a monounsaturated 3-OH FAEE. In some embodiments, unsaturated α,ω-diacids or unsaturated α,ω-diacid esters may be monounsaturated. Such monounsatured am-diacid esters may be half-acid esters, such as half-acid methyl or ethyl esters. In other embodiments, the monounsaturated α,ω-diacid ester may be a diester, such as a methyl diester or an ethyl diester. In some embodiments, the fatty acid derivative may include odd-numbered carbon chain, methyl-branching, or combinations thereof.

II. Reagents

In view of the variety of fatty acid derivative starting materials provided by the organisms disclosed herein, access to valuable organic products can be readily achieved. In general, subsequent organic transformations encompass one or more post-biosynthesis manipulation(s). In accordance with some embodiments, the reagent may be non-enzymatic. In one embodiment, the reagent is a protic acid. Examples of a protic acid include, but are not limited to, hydrochloric acid, sulfuric acid, and phosphoric acid. In another embodiment, the reagent is a recoverable resin acid. In other embodiments, the reagent is a Lewis acid. In some such embodiments, the Lewis acid may be an organostannane transesterification catalyst, magnesium, copper or zinc salts, silver triflate, and zeolites. Examples of Lewis acids include, without limitation, LiBr, $MgBr_2$, CsBr, $ZnBr_2$, $ZnCl_2$, CuBr, $Cu(CF_3SO_4)_2$, $BF_3.OEt_2$, KBr, $TiCl_4$, $SnCl_2$, $ScCl_3$, $VC_{13}$, $AlCl_3$, $InCl_3$, $Al_2CO_3$, $CeCl_3$, $Ag_2O$, $ZnClO_4$, $LiClO_4$, $Ti\{OCH(CH_3)_2)\}_4$ and any complexes and combination thereof. In still other embodiments, the reagent may be a peptide coupling agent. In some such embodiments, the peptide coupling agent may be compatible with aqueous systems that facilitate reactions directly in a culture broth. Thus, for example, such reagents may include water-soluble carbodiimide reagents. Coupling agents may include, without limitation, carbodiimdies such as N,N-dicyclocarbodiimide (DCC), N-(3-dimethylaminopropyl)-N'-ethylcarbonate (EDC), which may be optionally used with an acyl activating agent such as hydroxybenzotriazole (HOBt), phosphonium and uronim reagents such as benzotriazol-1-yl oxy-tris (dimethylamino) phosphonium hexafluorophosphate (BOP) or its tris-pyrrolidine variant (PyBOP), O-benzotriazol-1-yl-N,N,N-2-tetramethyluronium hexafluorophosphate (HBTU), or O-pyridotriazolyl variant (HATU), or oxime based reagents such as ethyl cyano(hydroxyimino) acetate-O2)-tri-(1-pyrrolidinyl)-phosphonium hexafluorophosphate (PyOxim) or its dimethylamino-morpholino variant (COMU).

III. Lactones

In some embodiments the lactone is a gamma-lactone (γ-lactone), a delta-lactone (δ-lactone), or combinations thereof. In some embodiments, the total carbon count of such products may be $C_8$ to $C_{18}$. By way of example, silver triflate has been utilized in the direct lactonization of unsaturated fatty acids as indicated in Scheme I below (see, e.g., Goossen et al. (2010) *Green Chem.* 12:197-200).

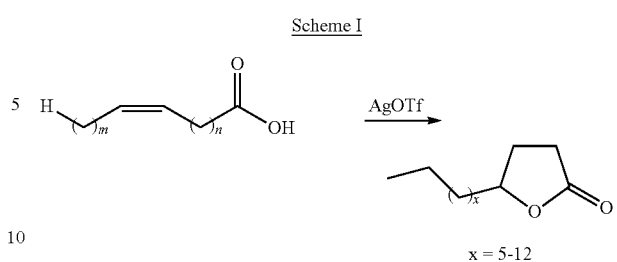

Scheme I x = 5-12

Protic acids have also been indicated to provide lactone products (see, e.g., Isbell et al. (1997) *J. Am. Oil Chemists Soc.* 74(2):153-158). In some embodiments, access to γ- and δ-lactones, both saturated and unsaturated may be accessible from, for example, 3-hydroxy substituted fatty acid derivatives via dehydration and deconjugative lactonization, as indicated in Scheme II below.

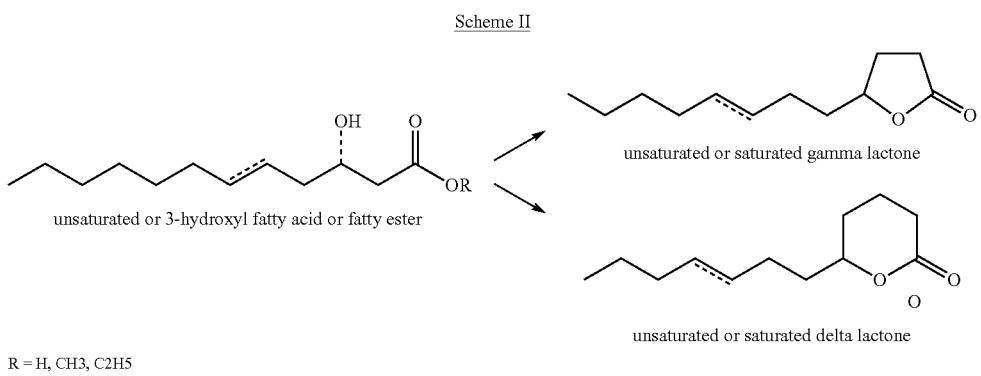

Scheme II unsaturated or 3-hydroxyl fatty acid or fatty ester

R = H, CH3, C2H5 unsaturated or saturated gamma lactone unsaturated or saturated delta lactone

Gamma lactones are particularly accessible from 3-hydroxy saturated and unsaturated fatty acid derivatives via ring expansion of the corresponding beta-lactone upon treatment with a Lewis acid (see, e.g., Mulzer et al. (1979) *Angew. Chemie Int. Ed. Engl.*, 18:793-794). Beta lactone access from 3-hydroxy fatty acid derivatives may be achieved by treatment of the 3-hydroxy acid with arylsulfonyl chloride/pyridine. In alternative embodiments, a beta lactone functionality may be built into the biosynthetic sequence. Under mild conditions, such as magnesium bromide at room temperature, beta lactones can undergo Lewis acid catalyzed dyotropic rearrangement (driven by release of ring strain) to the corresponding gamma lactone, as indicated in Scheme III below.

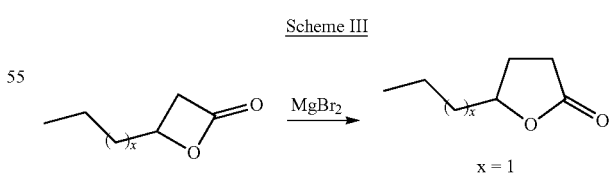

Scheme III x = 1

In some embodiments, the lactone is a $C_8$ to $C_{18}$ macrolactone. Macrolactone products may include dilactone products. Thus, in some embodiments, the starting material to macrolactone products may include saturated or monounsaturated omega hydroxy (ω-OH) acids or diacids, or half-acid esters. Scheme IV below shows an example of a macrolactone product with two ester functionalities derived from a diacid.

Scheme IV

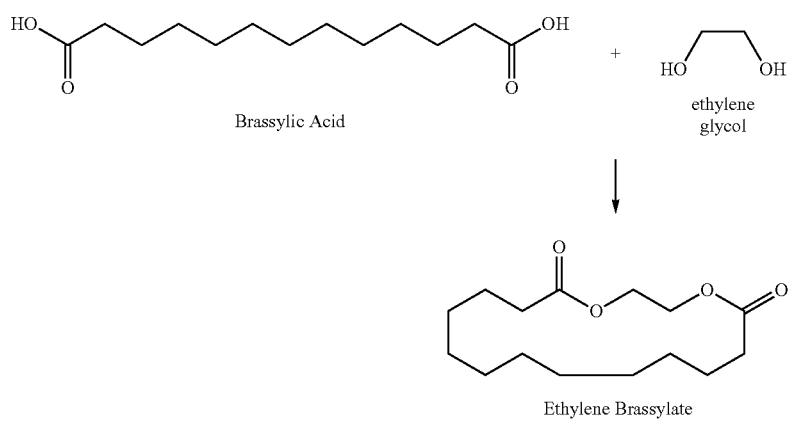

Ethylene Brassylate

One challenge in macrolactonization has been the minimization of undesired polymer pathways. One way to overcome such side reactions is to perform at high dilution. In some embodiments, fatty acid derivative bio-production with product secretion may naturally provide sufficiently dilute conditions amenable to directly carrying out macrolactonization via reagent introduction directly into a culture broth. By way of example, methods disclosed herein may provide for the biosynthetic production of an ω-hydroxy fatty acid by culturing a non-naturally occurring organism, followed by adding a water soluble peptide coupling agent directly into the culture broth. The reagent employed in the macrolactonization may be any of the aforementioned peptide coupling reagents (supra). Other reagents to effect such transformations include, acetic anhydride, pentafluorophenol, 2,4-dichlorobenzoyl chloride, and 2,4,6-trichlorobenzoyl chloride, using the so-called Yamaguchi method (see, e.g., Inanaga et al. (1989) *M. Bull. Chem. Soc. Jpn.* 1979: 52). Several approaches to macrolactones from ω-hydroxy fatty acids have been described (see, e.g., U.S. Pat. No. 4,014,902). Scheme V below shows an exemplary macrolactonization of an unsaturated ω-hydroxy fatty acid (or ester) that may be accessible via any of the aforementioned reagents and methods.

Scheme V

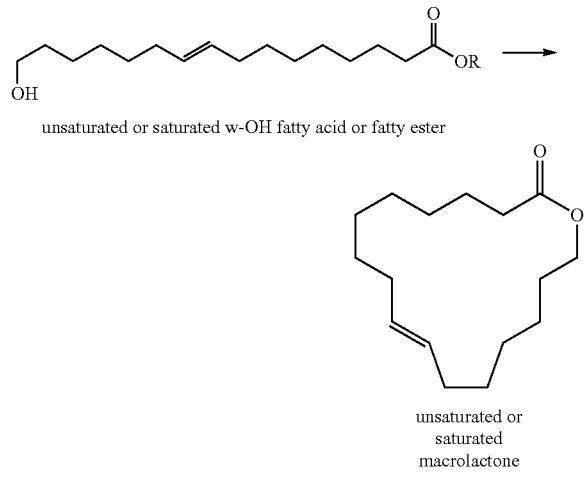

R = H, CH3, C2H5

In some embodiments, a polymeration and/or depolymeration approach can be employed to access macrolactone structures (see, e.g., Spanagel et al. (1935) *J. Am. Chem. Soc.*, 57:929-934). This technique can provide a greener alternative to solvent intensive high dilution conditions typically employed in macrolactonization reactions. Scheme VI below shows a known process in which bengalene acid is converted to isoambrettolide (cis/trans mixture) by action of potassium glycolate in ethylene glycol. Without wishing to be bound by theory, it is not known whether acetate removal provides a transient monomeric species prior to polymer formation. Moreover, under the reaction conditions, the polymer is also a transient species that is converted to the monomeric lactone structure which is readily drawn out of the reaction mixture under distillation.

Scheme VI

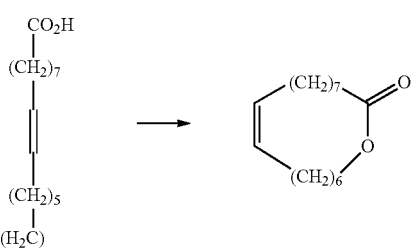

By way of further example, cis-9 ω-hydroxy hexadecenoic acid may be reacted with excess anhydrous acetic acid to afford the corresponding acetate derivative. The acetate derivative is then treated with sodium methoxide in a glycerol solvent resulting in a similar reaction as indicated in Scheme VI to provide the cis-9 isomer of ambrettolide. The cis-9 isomer ambrettolide can be continuously removed under vacuum distillation with concomitant removal of glycerol. Removal of glycerol from the distillate through phase separation results in a high purity cis-9 isomer of ambrettolide.

In still further embodiments, macrocyclic lactones may be accessed via their glyceryl esters (see, e.g., U.S. Pat. No.

2,234,551). Thus, heating the glyceryl ester of an ω-hydroxy fatty acid in glycerol allows for ω-distillation of a macrolactone product and glycerol solvent. The distillate is washed with water to afford a purified macrolactone product.

IV. Macrocyclic Ketones

In some embodiments, biosynthetic diacid, half-acid esters, or diesters, may be converted to corresponding macrocyclic ketones. Diesters may be converted to a cyclic hydroxy ketone product via acyloin condensation and, optionally, the hydroxy group may be reduced to provide a macrocyclic ketone (see, e.g., U.S. Pat. No. 3,963,571). Another method to produce macrocyclic ketones is by the Dieckmann condensation in a gas phase (see, e.g., U.S. Pat. No. 7,247,753). In some embodiments, the Dieckmann approach provides access to odd-chain carbon number ring sizes from even-chain fatty acid derivatives via decarboxylation mechanisms. Scheme VII below shows the general transformation that may be effected with diester, diacid, or half-acid ester starting materials.

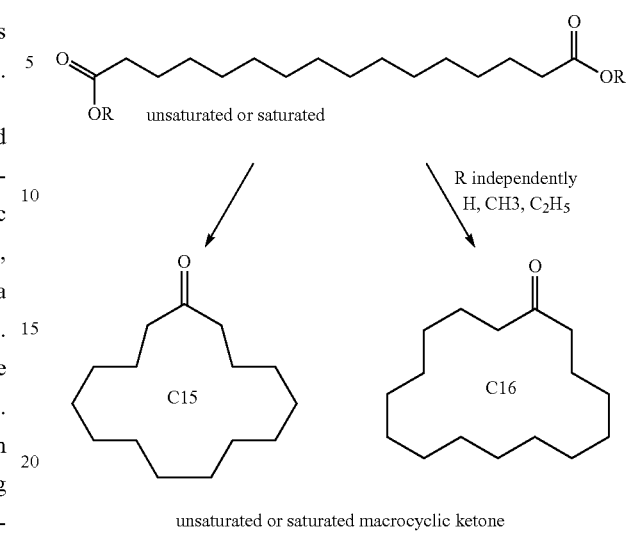

Scheme VII

General reactions indicating macrolactonization and macrocyclic ketone production generically are shown below in Scheme VIII and Scheme IX.

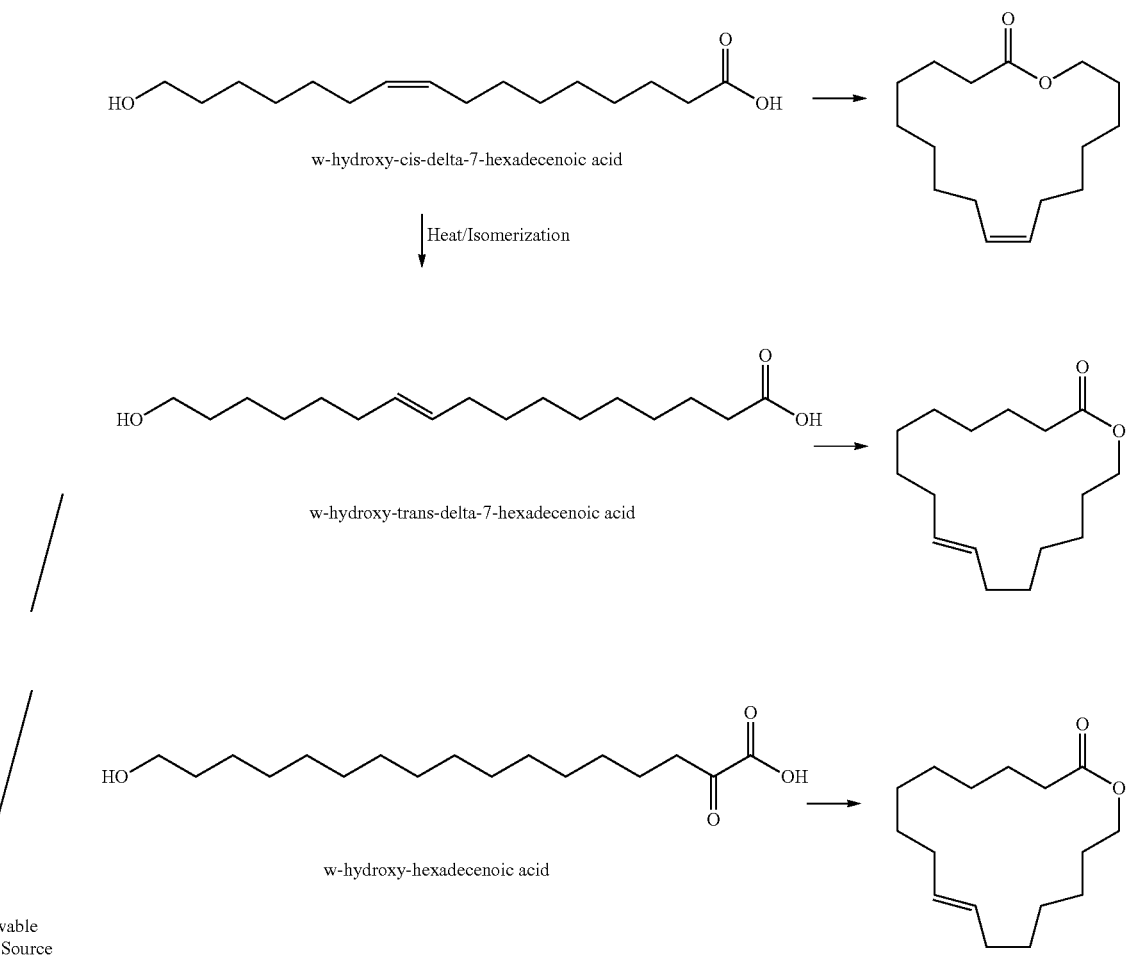

Scheme VIII

-continued
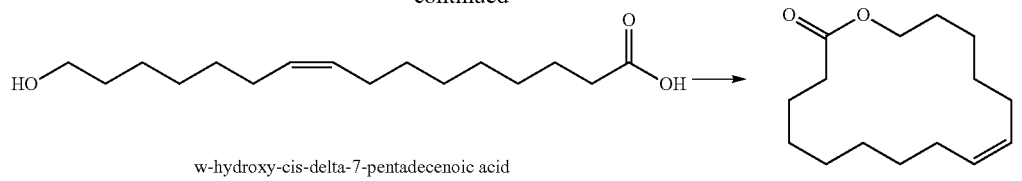
w-hydroxy-cis-delta-7-pentadecenoic acid
Heat/isomerization
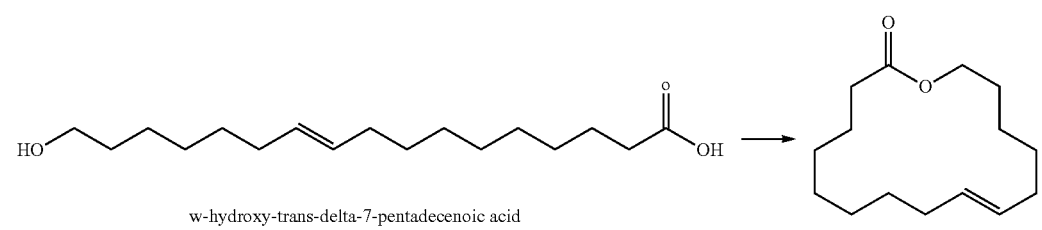
w-hydroxy-trans-delta-7-pentadecenoic acid
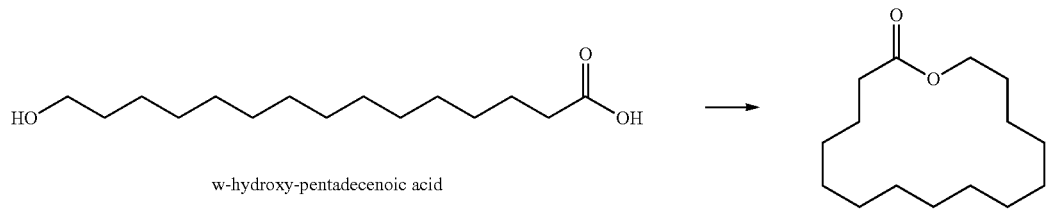
w-hydroxy-pentadecenoic acid
Scheme IX
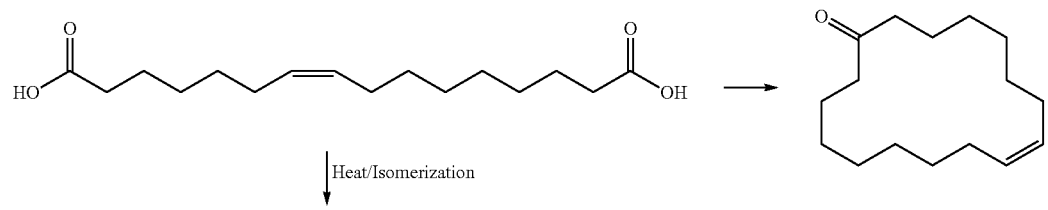
Heat/Isomerization
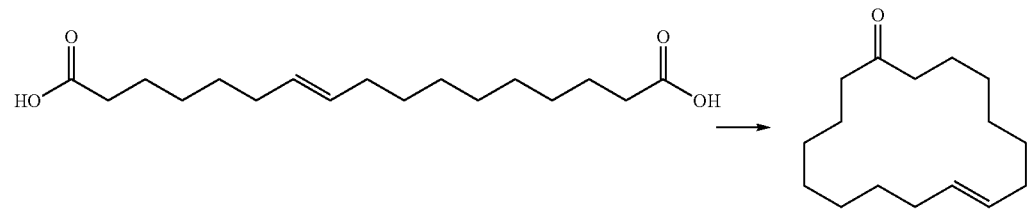
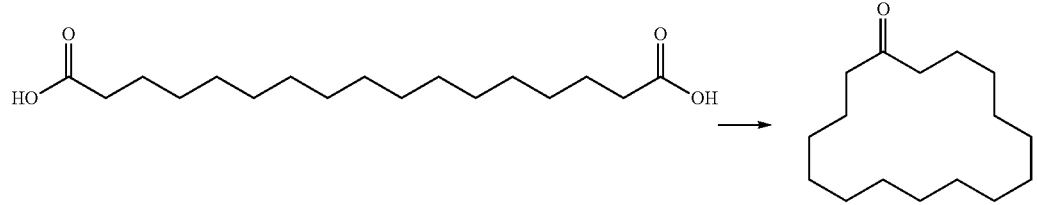

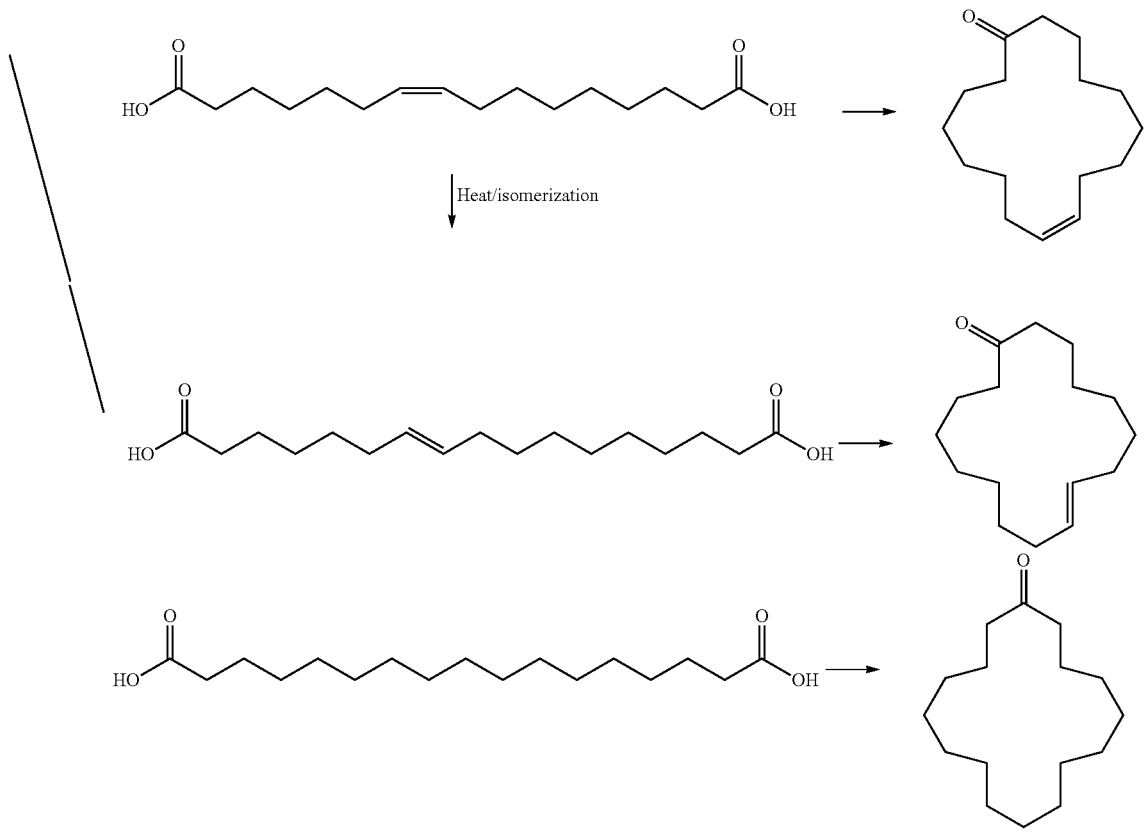

In some embodiments, target products obtained using the processes/methods disclosed herein may include fragrance lactones, such as the γ-lactones (e.g., γ-dodecalactone, tetradecalactone, rundecalactone, γ-decalactone, and γ-nonalactone) the δ-lactones (e.g., δ-dodecalactone, δ-tetradecalactone, δ-undecalactone, δ-decalactone, and δ-nonalactone), and the macrolactones (e.g., ambrettolide, iso-ambrettolide, dihydroambrettolide, habanolide (globalide), exaltolide (thibetolide) (cyclopentadecanolide), etc.) as well as other macrocyclic ketone fragrances, such as, romanone (exaltone, cyclopentadecanone), muscone, civetone, and the like.

V. Additional And Supplemental Methods

Additional and supplementary methods and processes for the preparation of macrocyclic compounds include condensation of difunctional compounds and subsequent thermal depolymerization in the presence of catalysts. The thermal depolymerization may be carried out in a solvent of the formula I:

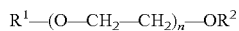

where $R^1$ and $R^2$ represent identical or different aliphatic hydrocarbon radicals having 1 to 6 carbon atoms with or without functional groups and having number average molecular weights (Mn) from 500 to 3,000, from which the value of n follows, at a pressure of less than 50 hPa and at a temperature of 200° C. to 300° C., 5 to 1,000 parts by weight of solvent being used per part by weight of the condensed difunctional compound (see, e.g., U.S. Pat. No. 5,717,111).

The high-boiling medium used for the thermal depolymerization encompasses polyethylene glycol dialkyl ethers having number average molecular weights (Mn) of between about 500 and 3,000. In one embodiment, the polyethylene glycol dialkyl ethers have number average molecular weights (Mn) of between about 1,000 and 2,000. The terminal OH groups of the polyethylene glycol dialkyl ethers are etherified with $C_{1-6}$ alkyl groups. The alkyl groups $R^1$ and $R^2$ etherifying the polyglycol can be, for example, methyl, ethyl, isopropyl, n-propyl, n-butyl or sec-butyl groups. The alkyl groups $R^1$ and $R^2$ may be further substituted with functional groups, wherein the functional groups may not participate in polymerization. Mixtures of different polyethylene glycol dialkyl ethers and of polyethylene glycol dialkyl ethers etherified by different alkyl groups may be used. 5 to 1,000 parts by weight of polyethylene glycol dialkyl ether, preferably from 10 to 100 parts by weight, may be used per 1 part by weight of the condensed difunctional compound.

In the depolymerization and cyclization of the linear oligomers, conventional catalysts can be employed, such as alkali metals and salts thereof, including but not limited to, magnesium salts, manganese salts, cadmium salts, iron salts, cobalt salts, tin salts, lead salts, aluminum salts and titanium salts. The amount of the catalyst, depending on the corresponding type used, is between about 0.1 to 20% by weight. In one embodiment, the amount of catalyst is between about 0.5 and 10% by weight, based on 100% by weight of the condensed difunctional compound. In another embodiment, the process is first initiated by the condensation of difunctional compounds, which may be performed according to conventional methods at elevated temperatures with or without catalyst. In one embodiment, the α,β-hydroxycarboxylic acid or α,β-dicarboxylic acid or ester is reacted with a glycol. The alcohol or the water formed in this process may be distilled off or removed using an entrainer or with the aid of a slight vacuum.

The methods include the depolymerization of linear polyesters accompanied by ring closure to form macrocyclic compounds. Polyesters that can be used in this process are obtained by conventional methods as known by those of skill in the art and are derived from conventional dicarboxylic acids, diols and hydroxymonocarboxylic acids. In one embodiment, the dicarboxylic acids are aliphatic and are saturated or contain olefinic unsaturation and are branched or straight-chain. In another embodiment, the aliphatic dicarboxylic acids contain from 3 up to about 18 carbon atoms. In still another embodiment, the aliphatic dicarboxylic acids contain from about 8 to 14 carbon atoms. Useful dicarboxylic acids include, but are not limited to, malonic acid, maleic acid, succinic acid, glutaric acid, adipic acid, pimelic acid, azelaic acid, sebacic acid, undecanedioic acid, dodecanedioic acid, brassylic acid, and pentadecanedioic acid. Mixtures of two or more dicarboxylic acids may also be used. In another embodiment, the polyesters are derived from aromatic or alicyclic dicarboxylic acids.

Polyesters can be derived from diols which are primarily aliphatic diols having from 2 to 12 carbon atoms. In one embodiment, the aliphatic diols have 2 to 6 carbon atoms. In another embodiment, the diols are saturated and straight-chain. In still another embodiment, the diols are saturated and branched. Useful diols include, but are not limited to, ethylene glycol; 1,2- or 1,3-propanediol; 1,2-, 1,3-, or 1,4-butanediol; 1,6-hexanediol; 3-methyl-1,5-pentanediol; 2,3-dimethyl-2,3-butanediol; 1,8-octanediol; 2-ethylhexanediol; 1,10-decanediol; 1,12-dodecanediol; diethylene glycol; and triethylene glycol. Alicyclic diols such as 1,4-cyclohexadimethanol may also be used.

Polyesters can also be derived from ethylene glycol and di-, tri- and tetraethylene glycol. Polyesters can also be derived from hydroxymonocarboxylic acids including, but are not limited to, 15-hydroxypentadecanoic acid, 16-hydroxyhexadecanoic acid, 10-oxa-16-hydroxyhexadecanoic acid, 11-oxa-16-hydroxyhexadecanoic acid, 12-oxa-16-hydroxyhexadecanoic acid, 10-thia-16-hydroxyhexadecanoic acid, 11-thia-16-hydroxyhexadecanoic acid, and 12-thia-16-hydroxyhexadecanoic acid.

Some condensed difunctional compounds that are suitable for depolymerization and cyclization have been described (see, e.g., U.S. Pat. No. 4,709,058). The condensed difunctional compound may be continuously transferred into a reactor, into which the high-boiling medium is introduced together with the catalyst component. The depolymerization and cyclization take place at high temperatures. In one embodiment, the depolymerization and cyclization take place at about 200° C. to 300° C. and a vacuum of less than 50 hPa. In another embodiment, the depolymerization and cyclization take place at about 220° C. to 265° C. and a vacuum of less than 50 hPa. Under these conditions, the target product distills over, the glycol (e.g., ethylene glycol) originating from the depolymerization or else a deliberate excess of glycol entraining the cyclic component. After phase separation, the separated glycol can be fed back to the condensation at the beginning of the reaction. Numerous macrocyclic compounds can be made by this process including, but not limited to, esters, lactones, lactams, etherlactones, dilactones and etherdilactones. This process is suitable for the preparation of macrocyclic esters and lactones having 6 to 20, or more particularly 8 to 15 carbon atoms since these compounds can be produced in relatively pure form which is advantageous for their use as perfumes.

Examples of macrocyclic compounds that can be produced by the depolymerization process include, but are not limited to 3,6,9-tridecamethylene malonate, dodecamethylene malonate, decamethylene malonate, ethylene suberate, ethylene azelate, 3-oxa-pentamethylene azelate, 3-methylpentamethylene sebacate, ethylene undecanedioate, ethylene dodecanedioate, ethylene brassylate, ethylene-alpha-methylbrassylate, ethylene-alpha,alpha-dimethylbrassylate, ethylene-alpha-ethylbrassylate, pentadecanolide, 12-oxa-pentadecanolide, 12-thia-pentadecanolide, hexadecanolide, 10-oxa-hexadecanolide, 11-oxa-hexadecanolide, 11-thia-hexadecanolide, and 12-oxa-hexadecanolide. The process can make ethylene brassylate by the depolymerization of polyethylene brassylate. Similarly, the process can make ethylene dodecanedioate by the depolymerization of polyethylene dodecanedioate (see, e.g., U.S. Pat. No. 5,717,111, supra).

EXAMPLES

The following example further illustrates the disclosure but should not be construed as in any way limiting its scope.

Example: Experimental Procedure for Macrolactonization

A mixture (30 g) containing 16-hydroxy-hexadecanoic acid and 16-hydroxy-7(Z)-hexadecenoic acid (obtained from fermentation) and ethylene glycol (60 mL) is heated to boiling, and ethylene glycol is slowly distilled over 4 hours to remove water. Tetrabutyl titanate (0.5 g) is added to the resulting mixture of ethylene glycol esters and hydroxyl acid oligomer esters in ethylene glycol. This is then slowly added over 4 hours to a reactor containing polyethylene glycol dimethyl ether (50 g, 1500-2000 Mn) at 250 C and 10 torr vacuum. The macrolactones co-distill with the ethylene glycol during this addition. Extraction of the distillate with cyclohexane and water washing yields a cyclohexane solution of the macrolactones. Concentration affords the crude macrolactones. Vacuum distillation yields a refined mixture of 16-hexadecalactone and 16-7(Z)-hexadecelactone.

As is apparent to one of skill in the art, various modifications and variations of the above aspects and embodiments can be made without departing from the spirit and scope of this disclosure. Such modifications and variations are within the scope of this disclosure.

What is claimed is:
1. A chemo-enzymatic process for producing a macrolactone selected from the group consisting of: 16-hexadecalactone and 16-7(Z)-hexadecalactone, the method comprising:
culturing a recombinant *Escherichia coli* (*E. coli*) comprising a modified fatty acid biosynthetic pathway, wherein the modified fatty acid biosynthetic pathway comprises an exogenous thioesterase selected from the group consisting of: fatB, obtained from *Arabidopsis thaliana*, and fatB3, obtained from *Cuphea hookeriana*; an endogenous mutated tesA; and an omega-hydroxylase or oxygenase, obtained from *Myobacterium marinum* M which are overexpressed,
wherein the omega-hydroxylase or oxygenase generates an omega-hydroxy fatty acid (ω-OH FA), wherein the ω-OH FA is 16-hydroxy-hexadecanoic acid or 16-hy- droxy-7(Z)-hexadecenoic acid, and wherein the culturing is performed with a carbon-based feedstock; and contacting the 16-hydroxy-hexadecanoic acid or the 16-hydroxy-7(Z)-hexadecenoic acid ex-vivo with a Lewis acid reagent under conditions sufficient to produce the macrolactone selected from the group consisting of 16-hexadecalactone and 16-7(Z)-hexadecelactone.

2. The chemo-enzymatic process of claim 1, wherein said modified fatty acid biosynthetic pathway further comprises a desaturase which is overexpressed to increase unsaturated fatty acid derivatives produced by said recombinant *E. coli*.

3. The method of claim 1, further comprising isolating the 16-hydroxy-hexadecanoic acid or 16-hydroxy-7(Z)-hexadecenoic acid prior to the contacting step.

4. The method of claim 1, wherein the 16-hydroxy-hexadecanoic acid or 16-hydroxy-7(Z)-hexadecenoic acid is secreted from said recombinant *E. coli* and the contacting step is performed without isolating the 16-hydroxy-hexadecanoic acid or 16-hydroxy-7(Z)-hexadecenoic acid from the culturing step.

5. The method of claim 1, wherein the contacting step comprises dehydration, lactonization, or combinations thereof.

6. The method of claim 1, wherein said carbon-based feedstock comprises a simple carbon source.

7. The method of claim 1, wherein said carbon-based feedstock is renewable.

8. The method of claim 1, wherein the Lewis acid comprises a tertbutyl titanate Lewis acid.

* * * * *